US008003324B2

(12) United States Patent
Dudley, Jr.

(10) Patent No.: US 8,003,324 B2
(45) Date of Patent: Aug. 23, 2011

(54) MODULATION OF SODIUM CHANNELS BY NICOTINAMIDE ADENINE DINUCLEOTIDE

(75) Inventor: Samuel C. Dudley, Jr., Chicago, IL (US)

(73) Assignees: U.S. Department of Veterans Affairs, Washington, DC (US); Emory University, Atlanta, GA (US)

( * ) Notice: Subject to any disclaimer, the term of this patent is extended or adjusted under 35 U.S.C. 154(b) by 116 days.

(21) Appl. No.: 12/289,005

(22) Filed: Oct. 17, 2008

(65) Prior Publication Data

US 2009/0105181 A1    Apr. 23, 2009

Related U.S. Application Data

(60) Provisional application No. 60/960,883, filed on Oct. 18, 2007.

(51) Int. Cl.
*C12Q 1/68* (2006.01)
*C07H 19/207* (2006.01)
*C12P 19/36* (2006.01)

(52) U.S. Cl. .......................... 435/6; 536/26.24; 435/90

(58) Field of Classification Search ........................ None
See application file for complete search history.

(56) References Cited

U.S. PATENT DOCUMENTS

| 5,668,114 | A * | 9/1997 | Birkmayer ....................... 514/52 |
| 6,833,371 | B2 | 12/2004 | Atkinson et al. |
| 7,094,600 | B2 | 8/2006 | Wang |
| 7,226,950 | B2 | 6/2007 | Choi et al. |
| 2005/0202093 | A1 | 9/2005 | Kohane et al. |
| 2007/0212723 | A1 | 9/2007 | Dudley et al. |

FOREIGN PATENT DOCUMENTS

| WO | WO-96/19225 | 6/1996 |
| WO | WO 2007/098065 A1 | 7/2009 |
| WO | WO 2010/129964 A1 | 11/2010 |

OTHER PUBLICATIONS

Sanyal et al. Circulation, Oct. 16, 2007. 116(16) S185-S186, Abstract 941.*
Krebs et al. (1999). "Na+ translocation by the NADH:ubiquinone oxidoreductase (complex I) from *Klebsiella pneumoniae*." Molecular Microbiology 33(2):590-598.
Udagawa et al. (1986). "Generation of Na+ electrochemical potential by the Na+-motive NADH oxidase and Na+/H+ antiport system of a moderately halophilic Vibrio costicola." J. Biol. Chem. 261(6):2616-2622.
Brugada P, Brugada J. Right bundle branch block, persistent ST segment elevation and sudden cardiac death: a distinct clinical and electrocardiographicsyndrome. A multicenter report. *J Am Coll Cardiol.* 1992;20:1391-1396.
Kadish, A. et al. 2006. Patients with recently diagnosed nonischemic cardiomyopathy benefit from implantable cardioverter-defibrillators. *J. Am Coll. Cardiol.* 47:2477-2482.

Amin AS, Verkerk AO, Bhuiyan ZA, Wilde AAM, Tan HL. Novel Brugada syndrom-causing mutation in ion-conducting pore of cardiac Na_ channel does not affect ion selectivity properties. *Acta Physiol Scand.* 2005;185:291-301.
Baroudi G, Napolitano C, Priori SG, Del Bufalo A, Chahine M. Loss of function associated with novel mutations of the SCN5A gene in patients with Brugada syndrome. *Can J Cardiol.* 2004;20:425-430.
Baroudi G, Acharfi S, Larouche C, Chahine M. Expression and Intracellular localization of an SCN5A double mutant R1232W/T1620M implicated in Brugada syndrome. *Circ Res.* 2002;90:e11-e16.
Baroudi G, Pouliot V, Denjoy I, Guicheney P, Shrier A, Chahine M. Novel mechanism for Brugada syndrome: Defective surface localization of an SCN5A mutant (R1432G). *Circ Res.* 2001;88:e78-e83.
Vatta M, Dumaine R, Antzelevitch C, Brugada R, Li H, Bowles NE, Nademanee K, Brugada J, Brugada P, Towbin JA. Novel mutations in domain I of SCN5A cause Brugada syndrome. *Mol Genet Metab.* 2002;75:317-324.
London B, Michalec M, Mehdi H, Zhu X, Kerchner L, Sanyal S, Viswanathan PC, Pfahnl AE, Shang LL, Madhusudanan M, Baty CJ, Lagana S, Aleong R, Gutmann R, Ackerman MJ, McNamara DM, Weiss R, Dudley SC Jr. Mutation in glycerol-3-phosphate dehydrogenase 1-like gene (GPD1-L) decreases cardiac Na_ current and causes inherited arrhythmias. *Circulation.* 2007;116:2260-2268.
Van Norstrand DW, Valdivia CR, Tester DJ, Ueda K, London B, Makielski JC, Ackerman MJ. Molecular and functional characterization of novel glycerol-3-phosphate dehydrogenase 1 like gene (GPD1-L) mutations in sudden infant death syndrome. *Circulation.* 2007;116:2253-2259.
Shen, W. et al. 2006. Involvement of glycerol-3-phosphate dehydrogenase in modulating the NADH/NAD+ ratio provides evidence of a mitochondrial glycerol-3-phosphate shuttle in Arabidopis. *Plant Cell.* 18:422-441.
Papadatos GA, Wallerstein PMR, Head CEG, Ratcliff R, Brady PA, Benndorf K, Saumarez RC, Trezise AEO, Huang CLH, Vandenberg JI, Colledge WH, Grace AA. Slowed conduction and ventricular tachycardia after targeted disruption of the cardiac sodium channel gene SCN5a. *Proc Natl Acad Sci U S A.* 2002;99:6210-6215.
Knollmann BC, Schober T, Petersen AO, Sirenko SG, Franz MR. Action potential characterization in intact mouse heart: steady-state cycle length dependence and electrical restitution. *Am J Physiol Heart Circ Physiol.* 2007;292:H614-H621.
Killeen MJ, Thomas G, Gurugn IS, Goddard CA, Fraser JA, Mahaut-Smith MP, Colledge WH, Grace AA, Huang CLH. Arrhythmogenic mechanisms in the isolated perfused hypokalaemic murine heart. *Acta Physiol.* 2007;189:33-46.
Zalba, G. et al. 2000. Vascular NADH/NADPH oxidase is involved in enhanced superoxide production in spontaneously hypertensive rats. *Hypertension.* 35:1055-1061.
Javesghani, D. et al. 2002. Molecular characterization of a superoxide-generating NAD(P)H oxidase in the ventilator muscles. *Am. J. Respir. Crit. Care Med.* 165: 412-418.

(Continued)

*Primary Examiner* — Doug Schultz
(74) *Attorney, Agent, or Firm* — Dinesh Agarwal, P.C.

(57) ABSTRACT

The present invention relates to the use of oxidized nicotinamide adenine dinucleotide (NAD$^+$) or of its reduced form, NADH, as sodium channel modulators. The present invention also relates to the use of compositions containing NAD$^+$ or NADH to treat conditions associated with sodium channel current, such as arrhythmia. NAD$^+$ is found to increase sodium channel current, while NADH is found to decrease sodium channel current. Thus, conditions that are associated with decreased sodium channel current can be treated with NAD$^+$, while conditions that is associated with increased sodium channel current can be treated with NADH.

12 Claims, 13 Drawing Sheets

OTHER PUBLICATIONS

Zicha, S. Maltsev, V.A., Nattel, S., Sabbah, H.N. and Undrovinas, A.L. 2004. Posttranscriptional alterations in the expression of cardiac Na+ channel subunits in chronic heart failure. *J. Mol. Cell. Cardiol.* 37: 91-100.

Schreibmayer W, Dascal N, Lotan I, Wallner M, Weigl L. Molecular mechanism of protein kinase C modulation of sodium channel_-subunits expressed in Xenopus oocytes. *FEBS Lett.* 1991;291:341-344.

Ward, C.A., and Giles, W.R. 1997. Ionic mechanism of the effects of hydrogen peroxide in rat ventricular myocytes. *J. Physiol.* 500: 631-642.

Takeishi, Y., Jalili, T., Ball, N.A. and Walsh, R.A. 1999. Responses of cardiac protein kinase C isoforms to distinct pathological stimuli are differently regulated. *Circ. Res.* 85: 264-271.

Sharma, A. and Singh, M. 2001. Protein kinase C activation and cardioprotective effect of preconditioning with oxidative stress in isolated rat heart. *Mol. Cell. Biochem.* 219: 1-6.

Brawn, M.K., Chiou, W.J. and Leach, K.L. 1995. Oxidant-induced activation of protein kinase C in UC11Mg cells. *Free Radic. Res.* 22: 23-37.

Pfahnl AE, Viswanathan PC, Weiss R, Shang LL, Sanyal S, Shusterman V, Kornblit C, London B, Dudley SC Jr. A sodium channel pore mutation causing Brugada syndrome. *Heart Rhythm.* 2007;4:46-53.

Kyndt, F. et al. 2001. Novel SCN5A mutation leading either to isolated cardiac conduction defect or Brugada syndrome in a large French family. *Circulation.* 104:3081-3086.

Tipparaju SM, Saxena N, Liu SQ, Kumar R, Bhatnagar A. Differential regulation of voltage-gated K_ channels by oxidized and reduced pyridine nucleotide coenzymes. *Am J Physiol Cell Physiol.* 2005;288: C366-C376.

Tipparaju SM, Liu SQ, Barski OA, Bhatnagar A. NADPH binding to _-subunit regulates inactivation of voltage-gated K_ channels. *Biochem Biophys Res Commun.* 2007;359:269-276.

Heiner I, Eisfeld J, Halaszovich CR, Wehage E, Jungling E, Zitt C Luckhoff A. Expression profile of the transient receptor potential (TRP) family in neutrophil granulocytes: evidence for currents through long TRP channel 2 induced by ADP-ribose and NAD. *Biochem J.* 2003;371: 1045-1053.

Herson PS, Dulock KA, Ashford ML. Characterization of a nicotinamideadenine dinucleotide-dependent cation channel in the CRI-G1 rat insulinoma cell line. *J Physiol.* 1997;505:65-76.

Alvarez J, Camaleno J, Garcia-Sancho J, Herreros B. Modulation of $Ca_2$_-dependent K_transport by modifications of the NAD_/NADH ratio in intact human red cells. *Biochim Biophys Acta.* 1986;856: 408-411.

Zima AV, Copello JA, Blatter LA. Effects of cytosolic NADH/NAD_ levels on sarcoplasmic reticulum $Ca_2$_ release in permeabilized rat ventricular myocytes. *J Physiol.* 2004;555:727-741.

Park MK, Lee SH, Ho WK, Earm YE. Redox agents as a link between hypoxia and the responses of ionic channels in rabbit pulmonary vascular smooth muscle. *Exp Physiol.* 1995;80:835-842.

Aon MA, Cortassa S, Marban E, O'Rourke B. Synchronized whole cell oscillations in mitochondrial metabolism triggered by a local release of reactive oxygen species in cardiac myocytes. *J Biol Chem.* 2003;278: 44735-44744.

Di LF, Menabo R, Canton M, Barile M, Bernardi P. Opening of the mitochondrial permeability transition pore causes depletion of mitochondrial and cytosolic NAD_ and is a causative event in the death of myocytes in postischemic reperfusion of the heart. *J Biol Chem.* 2001; 276:2571-2575.

Choudhary G, Dudley SC Jr. Heart failure, oxidative stress, and ion channel modulation. *Congest Heart Fail.* 2002;8:148-155.

Pillai JB, Isbatan A, Imai Si, Gupta MP. Poly(ADP-ribose) polymerase-1-dependent cardiac myocyte cell death during heart failure is mediated by NAD_ depletion and reduced Sir2_ deacetylase activity. *J Biol Chem.* 2005;280:43121-43130.

Dzhanashiya PK, Vladytskaya OV, Salibegashvili NV. Efficiency and mechanisms of the antioxidant effect of standard therapy and refracterin in the treatment of chronic heart failure in elderly patients with postinfarction cardiosclerosis. *Bull Exp Biol Med.* 2004;138:412-414.

Shang LL, Pfahnl AE, Sanyal S, Jiao Z, Allen J, Banach K, Fahrenbach J, Weiss D, Taylor WR, Zafari AM, Dudley SC Jr. Human heart failure is associated with abnormal C-terminal splicing variants in the cardiac sodium channel. *Circ Res.* 2007;101:1146-1154, and Online Supplement (pp. 1-10).

Makielski JC, Farley A. Na_ current in human ventricle: implications for sodium loading and homeostasis. *J Cardiovasc Electrophysiol.* 2006;17: S15-S20.

Valdivia CR, Chu WW, Pu J, Foell JD, Haworth RA, Wolff MR, Kamp TJ, Makielski JC. Increased late sodium current in myocytes from a canine heart failure model and from failing human heart. *J Mol Cell Cardiol.* 2005;38:475-483.

Ajiro Y, Hagiwara N, Kasanuki H. Assessment of markers for idendifying patients at risk for life-threatening arrhythmic events in Brugada syndrome. *J Cardiovasc Electrophysiol.* 2005;16:45-51.

Gellens et al. Primary Structure and Functional Expression of the Human Cardiac Tetrodotoxin-Insensitive Voltage-Dependent Sodium-Channel. *Proceedings of the National Academy of Sciences of the United States of America* 89, 554-558 (1992).

Wang et al. Genomic organization of the human SCN5A gene encoding the cardiac sodium channel. *Genomics* 34, 9-16 (1996).

George et al. Assignment of the human heart tetrodotoxin-resistant voltage-gated Sodium channel alpha-subunit gene (SCN5A) to band 3p21. *Cytogenet. Cell Genet.* 68, 67-70 (1995).

Schott et al. Cardiac conduction defects associate with mutations in SCN5A. *Nat. Genet.* 23, 20-21 (1999).

Tan et al. A calcium sensor in the sodium channel modulates cardiac excitability. *Nature* 415, 442-447 (2002).

Zubay, Biochemistry, Chapter 10, part II Carbohydrate metabolism and chemical energy, p. 400-403 (1984).

Remington's Pharmaceutical Sciences, Mace Publishing Company, Philadelphia, Pa., 17th ed. (1985).

Alings, M. and Wilde A. "Brugada" Syndrome: Clinical Data and Suggested Pathophysiological Mechanism. *Circulation* 1999; 99:666-673.

Brugada J, Brugada R, Antzelevitch C et al. Long-term follow-up of individuals with the electrocardiographic pattern of right bundle-branch block and ST-segment elevation in precordial leads V1 to V3. *Circulation.* 2002;105:73-78.

Zhou, M. Diwu Z., Panchuk-Voloshina, N. and Haugland. A Stable Nonfluorescent Derivative of Resorufin for the Fluorometric Determination of Trace Hydrogen Peroxide: Applications in Detecting the Activity of Phagocyte NADPH Oxidase and Other Oxidases. *Analytical Biochemistry* 253 (1997) 162-168.

Mohanty, J.G., Jaffe, J.S., Schulman, E.S. and Raible, D.G.. A Highly Sensitive Fluorescent Micro-Assay of H2O Release from Activated Human Leukocytes Using a Dihydroxyphenoxazine Derivative. *Journal of Immunological Methods* 202 (1997) 133-141.

Liu M, Sanyal S, Gao G, Gurung IS, Zhu X, Gaconnet G, Kerchner LJ, Shang LL, Huang CLH, Grace A, London B, Dudley SC, Jr. Cardiac $Na^+$ current regulation by pyridine nucleotides. *Circ. Res.* 2009; 105:737-45, Supplemental Material (pp. 1-8), and Author manuscript Cir Res Oct. 2009; 105(8):737-745.

Shaw RM, Rudy Y. Ionic mechanisms of propagation in cardiac tissue: roles of the sodium and L-type calcium currents during reduced excitability and decreased gap junction coupling. *Circ. Res.* 1997; 81:727-41.

Shimizu W, Aiba T, Kamakura S. Mechanisms of disease: current understanding and future challenges in Brugada syndrome. *Nat Clin Pract Cardiovasc Med.* 2005; 2:408-14.

Andrukhiv A, Costa ADT, West I, Garlid KD. Opening of mito$K_{ATP}$ increases superoxide generation from complex I of the electron transport chain. *Am J Physiol Heart Circ Physiol.* 2006; 291:H2067-H2074.

Ide T, Tsutsui H, Kinugawa S, Utsumi H, Kang D, Hattori N, Uchida K, Arimura Ki, Egashira K, Takeshita A. Mitochondrial electron transport complex I is a potential source of oxygen free radicals in the failing myocardium. *Circ Res.* 1999; 85:357-63.

Mallat Z, Philip I, Lebret M, Chatel D, Maclouf J, Tedgui A. Elevated levels of 8-iso-prostaglandin F2a in pericardial fluid of patients with heart failure : a potential role for in vivo oxidant stress in ventricular dilatation and progression to heart failure. *Circulation.* 1998: 97:1536-9.

Hill MF, Singal PK. Right and left myocardial antioxidant responses during heart failure subsequent to myocardial infarction. *Circulation.* 1997; 96:2414-20 (11 pages).

Dhalla AK, Singal PK. Antioxidant changes in hypertrophied and failing guinea pig hearts. *Am J Physiol Heart Circ Physiol.* 1994; 266:H1280-H1285.

Brady N, Hamacher-Brady A, Westerhoff H, Gottlieb R. A wave of reactive oxygen species (ROS)-induced ROS release in a sea of excitable mitochondria. *Antioxid Redox Signal.* 2006; 8:1651-65.

Zorov DB, Filburn CR, Klotz LO, Zweier JL, Sollott SJ. Reactive oxygen species (ROS)-induced ROS release: a new phenomenon accompanying induction of the mitochondrial permeability transition in cardiac myocytes. *J Exp Med.* 2000; 192:1001-14.

Costa ADT, Pierre SV, Cohen MV, Downey JM, Garlid KD. cGMP signalling in pre- and post-conditioning: the role of mitochondria. *Cardiovasc Res.* 2008; 77:344-52.

Ogbi M, Chew CS, Pohl J, Stuchlik O, Ogbi S, Johnson JA. Cytochrome c oxidase subunit IV as a marker of protein kinase Ce function in neonatal cardiac myocytes: implications for cytochrome c oxidase activity. *Biochem J.* 2004; 382:923-32.

Clarke SJ, McStay GP, Halestrap AP. Sanglifehrin A Acts as a Potent Inhibitor of the Mitochondrial Permeability Transition and Reperfusion Injury of the Heart by Binding to Cyclophilin-D at a Different Site from Cyclosporin A. *J Biol Chem* 2002;277:34793-9.

Sato T, O'Rourke B, Marban E. Modulation of mitochondrial ATP-dependent $K^+$ channels by protein kinase C. *Circ Res.* 1998; 83:110-4.

O'Rourke B. Evidence for mitochondrial $K^+$ channels and their role in cardioprotection. *Circ Res.* 2004; 94:420-32, and Supplement (pp. 1-6).

Chen Q, Vazquez E, Moghaddas S, Hoppel C, Lesnefsky E. Production of reactive oxygen species by mitochondria. *J Biol Chem.* 2003; 278:36027-31.

Akar FG, Aon MA, Tomaselli GF, O'Rourke B. The mitochondrial origin of postischemic arrhythmias. *J Clin Invest.* 2005; 115:3527-35.

Murphy MP. How mitochondria produce reactive oxygen species. *Biochem J.* 2009; 417:1-13.

O'Rourke B, Ramza B, Marban E. Oscillations of membrane current and excitability driven by metabolic oscillations in heart cells. *Science.* 1994; 265:962-6.

Murray KT, Hu N, Daw JR, Shin HG, Watson MT, Mashburn AB, George AL Jr. Functional effects of protein kinase C activation on the human cardiac Na_ channel. *Circ Res.* 1997;80:370-376.

Zhou J, Yi J, Hu N, George AL Jr, Murray KT. Activation of protein kinase A modulates trafficking of the human cardiac sodium channel in Xenopus oocytes. *Circ Res.* 2000;87:33-38.

Hallaq et al. Quantitation of protein kinase A-mediated trafficking of cardiac sodium channels in living cells. Cardiovascular Research 72 (2006) 250-261.

Zhou J, Shin HG, Yi J, Shen W, Williams CP, Murray KT. Phosphorylation and putative ER retention signals are required for protein kinase A-mediated potentiation of cardiac sodium current. *Circ Res.* 2002;91: 540-546.

Zhang F, Jin S, Yi F, Xia M, Dewey WL, Li PL. Local production of O2 by NAD(P)H oxidase in the sarcoplasmic reticulum of coronary arterial myocytes: cADPR-mediated Ca2_ regulation. *Cell Signal.* 2008;20: 637-644.

Nitti et al. PKC signaling in oxidative hepatic damage. Molecular Aspects of Medicine 29 (2008) 36-42.

Bruzzone et al. Extracellular NAD+ regulates intracellular calcium levels and induces activation of human granulocytes. Biochem. J. (2006) 393, 697-704.

Romanello et al. Extracellular NAD1 Induces Calcium Signaling and Apoptosis in Human Osteoblastic Cells. Biochemical and Biophysical Research Communications 285, 1226-1231 (2001).

Budas & Mochly-Rosen. Mitochondrial protein kinase Cε (PKCε): emerging role in cardiac protection from ischaemic damage. Biochemical Society Transactions (2007) vol. 35, part 5, 1052-1054.

Silberman GA, Fan T-H, Liu H, Jiao Z, Xiao HD, Lovelock JD, Boulden B, Widder J, Fredd S, Bernstein KE, Wolska B, Dikalov S, Harrison DG, Dudley SCJr. Uncoupled cardiac nitric oxide synthase mediates diastolic dysfunction. *Circulation.* 2010; 121:519-28, and Supp. Data (21 pp.).

Sorescu D, Weiss D, Lassegue B, Clempus RE, Szocs K, Sorescu GP, Valppu L, Quinn MT, Lambeth JD, Vega JD, Taylor WR, Griendling KK. Superoxide production and expression of Nox family proteins in human atherosclerosis. *Circulation.* 2002; 105:1429-35.

Pacher P, Nivorozhkin A, Szabo C. Therapeutic effects of xanthine oxidase inhibitors: Renaissance half a century after the discovery of allopurinol. *Pharmacol Rev.* 2006; 58:87-114.

Kobayashi K, Neely JR. Control of maximum rates of glycolysis in rat cardiac muscle. *Circ Res.* 1979; 44:166-75.

Li Q, Hwang YC, Ananthakrishnan R, Oates PJ, Guberski D, Ramasamy R. Polyol pathway and modulation of ischemia-reperfusion injury in Type 2 diabetic BBZ rat hearts. *Cardiovasc Diabetol.* 2008; 7:33-44 (11 pages).

Moir AM, Zammit VA. Insulin-independent and extremely rapid switch in the partitioning of hepatic fatty acids from oxidation to esterification in starved-refed diabetic rats. *Biochem J.* 1995; 305:953-8.

van Raam B, Sluiter W, de Wit E, Roos D, Verhoeven A, Kuijpers T. Mitochondrial membrane potential in human neutropils is maintained by complex III activity in the absence of supercomplex organisation. *PLoS ONE.* 2008; 3:e2013 (12 pages).

Liang HL, Arsenault J, Mortensen J, Park F, Johnson CP, Nilakanta V. Partial attenuation of cytotoxicity and apoptosis by SOD1 in ischemic renal epithelial cells. *Apoptosis.* 2009; 14:1176-89.

Dikalova AE, Bikineyeva AT, Budzyn K, Nazarewicz RR, McCann L, Lewis W, Harrison DG, Dikalov SI. Therapeutic targeting of mitochondrial superoxide in hypertension. *Circ Res.* 2010; 107:106-16, and Online Supp. (12 pages).

Murphy E, Steenbergen C. Preconditioning: the mitochondrial connection. *Annu Rev Physiol.* 2007; 69:51-67.

Barth E, Stämmler G, Speiser B, Schaper J. Ultrastructural quantitation of mitochondria and myofilaments in cardiac muscle from 10 different animal species including man. *J Mol Cell Cardiol.* 1992; 24:669-81.

Boveris A, Oshino N, Chance B. The cellular production of hydrogen peroxide. *Biochem J.* 1972; 128:617-630.

Batandier C, Fontaine E, Keriel C, Leverve X. Determination of mitochondrial reactive oxygen species: methodological aspects. *J Cell Mol Med.* 2002; 6:175-87.

Panov A, Schonfeld P, Dikalov S, Hemendinger R, Bonkovsky HL, Brooks BR. The Neuromediator glutamate, through specific substrate interactions, enhances mitochondrial ATP production and reactive oxygen species generation in monsynaptic brain mitochondria. *J Biol Chem.* 2009; 284:14448-56.

Han D, Antunes F, Canali R, Rettori D, Cadenas E. Voltage-dependent anion channels control the release of the superoxide anion from mitochondria to cytosol. *J Biol Chem.* 2003; 278:5557-63.

Brown D, Aon MA, Akar FG, Liu T, Sorarrain N, O'Rourke B. Effects of 4'-chlorodiazepam on cellular excitation-constraction coupling and ischaemia-reperfusion injury in rabbit heart. *Cardiovasc Res.* 2008; 79:141-9.

Valdivia CR, Ueda K, Ackerman MJ, Makielski JC. GPD1L links redox state to cardiac excitability by PKC-dependent phosphorylation of the sodium channel SCN5A. *AJP—Heart and Circulatory Physiology.* 2009; 297:H1446-H1452.

Zelent B, Troxler T, Vanderkooi JM. Temperature dependence for fluorescence of β-NADH in glycerol/water solution and in trehalose/sucrose glass. *Journal of Fluorescence.* 2007; 17:37-42.

Liu M, Gaconnet G, London B, Dudley, Jr. S.C. A Central Role of Mitochondria in the Regulation of Sodium Current. Presentation at the Cardiac Electrophysiology Society, Orlando, Florida (Nov. 14, 2009) (1 page).

Yang H, Yang T, Baur JA, Perez E, Matsui T, Carmona JJ, Lamming D, Souza-Pinto NC, Bohr VA, Rosenzweig A, de Cabo R, Sauve A, Sinclair DA. Nutrient-sensitive mitochondrial NAD_ levels dictate cell survival. *Cell.* 2007;130:1095-1107.

Lin SJ, Guarente L. Nicotinamide adenine dinucleotide, a metabolic regulator of transcription, longevity and disease. *Curr Opin Cell Biol.* 2003;15:241-246.

Herbert JM, Augereau JM, Gleye J, Maffrand JP. Chelerythrine is a potent and specific inhibitor of protein kinase C. *Biochem Biophys ResCommun.* 1990;172:993-999.

Chao MD, Chen IS, Cheng JT. Inhibition of protein kinase C translocation from cytosol to membrane by chelerythrine. *Planta Med.* 1998;64: 662-663.

Frohnwieser B, Chen L, Schreibmayer W, Kallen R. Modulation of the human cardiac sodium channel alpha-subunit by cAMP-dependent protein kinase and the responsible sequence domain. *J Physiol* (London). 1997;498:309-318.

Glass DB, Lundquist LJ, Katz BM, Walsh DA. Protein kinase inhibitor-(6-22)-amide peptide analogs with standard and nonstandard amino acid substitutions for phenylalanine 10. Inhibition of cAMP-dependent protein kinase. *J Biol Chem.* 1989;264:14579-14584.

Shin HG, Murray KT. Conventional protein kinase C isoforms and cross-activation of protein kinase A regulate cardiac Na_ current. *FEBS Lett.* 2001;495:154-158.

Biswas S, DiSilvestre D, Tian Y, Halperin VL, Tomaselli GF. Calciummediated dual-mode regulation of cardiac sodium channel gating. *Circ Res.* 2009;104:870-878, and Supp. Material (10 pages).

Casini S, Verkerk AO, van Borren MM, van Ginneken AC, Veldkamp MW, de Bakker JM, Tan HL. Intracellular calcium modulation of voltage-gated sodium channels in ventricular myocytes. *Cardiovasc Res.* 2009;81:72-81.

Brisson D, Vohl M, St Pierre J, Hudson T, Gaudet D. Glycerol: a neglected variable in metabolic process? *Bioessays.* 2001;23.6:534-542.

Antzelevitch C, Brugada P, Borggrefe M, et al. Brugada syndrome: report of the second consensus conference: endorsed by the Heart Rhythm Society and the European Heart Rhythm Association. *Circulation.* 2005; 111 :659-670.

Brugada J, Brugada P. Further characterization of the syndrome of right bundle branch block, ST segment elevation, and sudden cardiac death. *J Cardiovasc Electrophysiol.* 1997; 8:325-331.

Grant AD. Electrophysiological basis and genetics of Brugada syndrome. *J Cardiovasc Electrophysiol.* 2005; 16:S3-7.

Chen Q, Kirsch GE, Zhang 0, et al. Genetic basis and molecular mechanism for idiopathic ventricular fibrillation. *Nature.* 1998; 392:293-296.

Priori SG, Napolitano C, Gasparini M, et al. Clinical and genetic heterogeneity of right bundle branch block and ST -segment elevation syndrome: A prospective evaluation of 52 families. *Circulation.* 2000; 102:2509-2515.

Valdivia CR, Tester OJ, Rok BA, et al. A trafficking defective, Brugada syndromecausing SCNSA mutation rescued by drugs. *Cardiovasc Res.* 2004; 62:53-62.

Brugada R, Brugada J, Antzeievitch G, et al. Sodium channel blockers identify risk for sudden death in patients with ST-segment elevation and right bundle branch block but structurally normal hearts. *Circulation.* 2000; 101:510-515.

Pollevick GO, Schimpf R, Aizawa Y, et al. Loss of function in calcium channel activity secondary to a mutation in CACNB2b modulates the clinical manifestation of a combined Brugada syndrome-hort aT phenotype. *Circulation.* 2006; 114:11-193 (Abstract—3 pages).

Yan GX, Antzelevitch C. Cellular basis for the Brugada syndrome and other mechanisms of arrhythmogenesis associated with ST-segment elevation. *Circulation.* 1999; 100:1660-1666.

Weiss R, Barmada MM, Nguyen T, et al. Clinical and molecular heterogeneity in the Brugada syndrome: a novel gene locus on chromosome 3. *Circulation.* 2002;105:707-713.

Walz AG, Demel RA, de Kruijff S, et al. Aerobic sn-glycerol-3-phosphate dehydrogenase from *Escherichia coli* binds to the cytoplasmic membrane through an amphipathic alpha-helix. *Biochem J.* 2002; 365:471-479.

Myerburg RJ, Castellanos A. Cardiac arrest and sudden cardiac death. In: P. ZD, Libby P, Bonow RO, et al., eds. *Braumwald's Heart disease: A textbook of cardiovascular medicine.* 7th ed. Phildadelphia: Elsevier Saunders; 2005:865-908 (Chapter 33).

Priori SG, Rivolta I, Napolitano C. Genetics of long QT, Brugada, and other channelopathies. In: P. ZD, Jalife J, eds. *Cardiac Electrophysiology. From Cell to Bedside.* 4th ed. Philadelphia: Saunders; 2004:462-470 (Chapter 50).

Sarkozy A, Brugada P. Sudden Cardiac Death and Inherited Arrhythmia Syndromes. J *Cardiovasc Electrophysiol.* 2005; 16:S8-20.

Mohler PJ, Schott JJ, Gramolini AO, et al. Ankyrin-B mutation causes type 4 long-QT cardiac arrhythmia and sudden cardiac death. *Nature.* 2003; 21:634-639.

Corrado 0, Thiene G. Arrhythmogenic right ventricular cardiomyopathy/dysplasia: clinical impact of molecular genetic studies. *Circulation.* 2006; 113:1634-1637.

Schwartz PJ, Priori SG, Dumaine R, et al. A molecular link between the sudden infant death syndrome and the long-QT syndrome. *N Engl J Med.* 2000;343:262-267.

Van Norstrand OW, Valdivia CR, Tester OJ, et al. Molecular and functional characterization of a novel GPD1-L mutations in sudden Infant Death Syndrome. Circulation 2007; 116-2253-2259.

Royer A, van Veen TA, Le Bouter S, et al. Mouse model of SCNSA-linked hereditary Lenegre's disease: age-related conduction slowing and myocardial fibrosis. *Circulation.* 2005; 111: 1738-1746.

Tan HL, Bink-Boelkens MT, Bezzina CR, et al. A sodium-channel mutation causes isolated cardiac conduction disease. *Nature.* 2001; 409:1043-1047.

Mihm MJ, Yu F, Cames CA, et al. Impaired myofibrillar energetics and oxidative injury during human atrial fibrillation. *Circulation.* 2001; 104:174-180.

Fukuda K, Davies SS, Nakajima T, et al. Oxidative mediated lipid peroxidation recapitulates proarrhythmic effects on cardiac sodium channels. *Circ Res.* 2005; 97:1262-1269.

Rubart M, Zipes DP. Mechanisms of sudden cardiac death. *J Clin Invest.* 200S; 115:2305-2315.

CAST. Preliminary report: effect of encainide and flecainide on mortality in a randomized trial of arrhythmia suppression after myocardial infarction. The Cardiac Arrhythmia Suppression Trial (CAST) Investigators. *N Engl J Med.* 1989; 321 :406-412.

* cited by examiner

Fig. 1
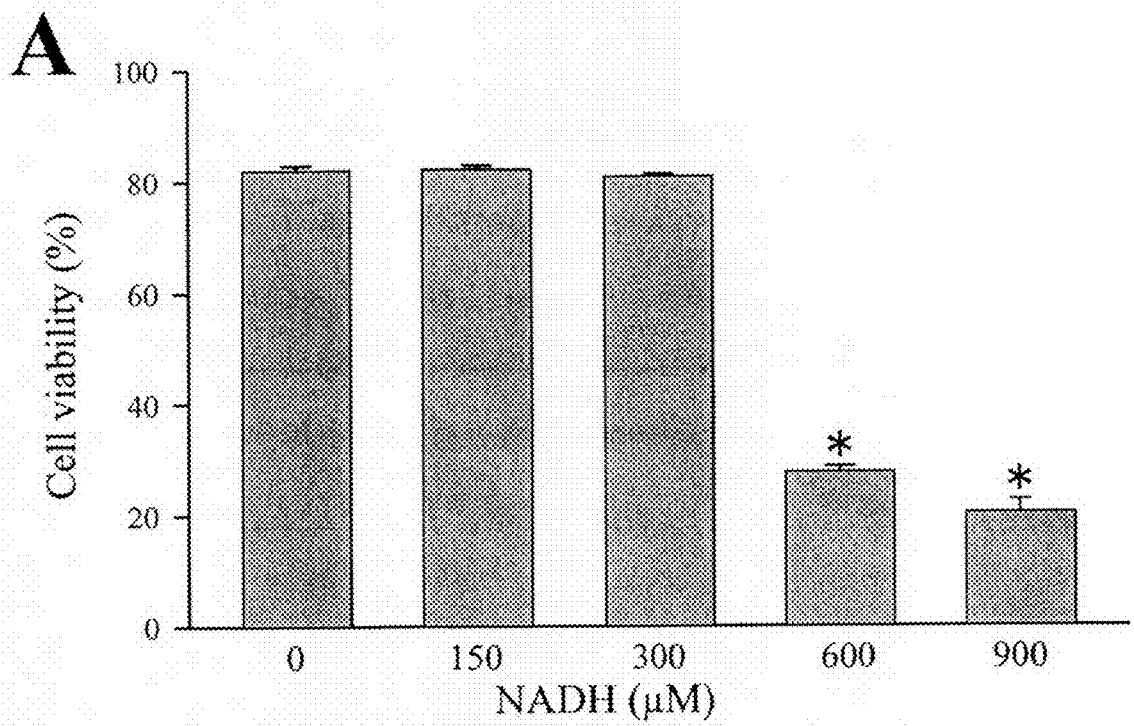
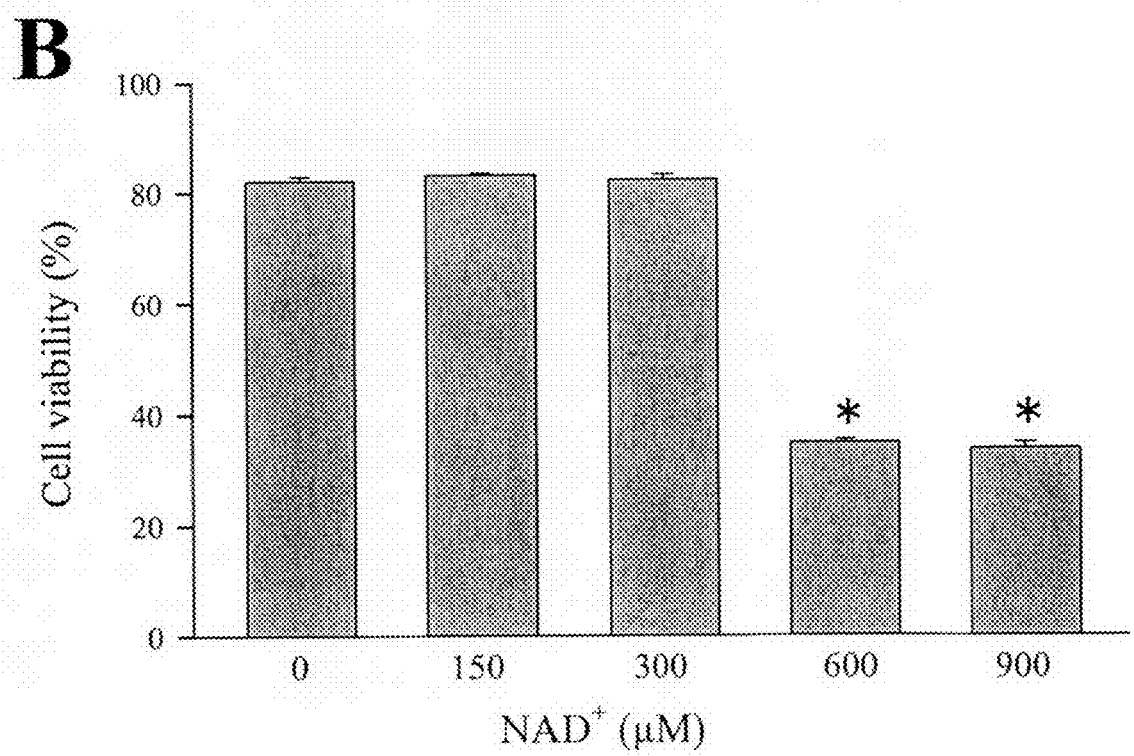

MODULATION OF SODIUM CHANNELS BY NICOTINAMIDE ADENINE DINUCLEOTIDE

This application claims the priority of U.S. Provisional Patent Application Ser. No. 60/960,883, filed Oct. 18, 2007, which is incorporated herein by reference.

The subject invention was made with government support under Grant Nos. R01 HL077398 and R01 HL073753, awarded by the National Institute of Health. The government has certain rights in this invention.

FIELD OF THE INVENTION

The present invention relates to the use of oxidized nicotinamide adenine dinucleotide (NAD+) or of its reduced form, NADH, as sodium channel modulators. The present invention also relates to the use of NAD+ or NADH to treat conditions associated with sodium channel current, such as arrhythmia.

BACKGROUND OF THE INVENTION

Voltage-gated sodium channels are pore-forming membrane proteins responsible for the initiation and propagation of action potentials in excitable membranes in nerve, skeletal muscle and heart cells. The controlled gating of sodium channels in response to membrane depolarization is necessary for normal electrical signaling and establishing of intercellular communication. The cardiac voltage-sensitive sodium ($Na^+$) channel is composed of α and β subunits. The gene encoding the α-subunit, SCN5A, has been cloned and found to consist of 28 exons spanning over 80 kb of DNA. The α-subunit (or its isoforms) contains four homologous repeated domains (D1-D4), each with six transmembrane segments (S1-S6). The α-subunit protein alone forms a functional channel when expressed in mammalian expression systems. The four repeated domains are hypothesized to assemble as a pseudotetrameric structure with the permeation pathway situated at the center. The protein is responsible for the rapid influx of sodium ions that initiate and propagate action potential in the heart and the large peak sodium influxes responsible for excitability and conduction in myocardium and special conduction tissues.

The human voltage-gated cardiac Sodium channel α-subunit, referred to as Nav1.5, which is encoded by the gene SCN5A, is by far the most abundant Sodium channel protein in the human heart. The SCN5A gene has been cloned and characterized in 1992 by Gellens et al. (Proceedings of the National Academy of Sciences of the United States of America 89:554-558 (1992)). SCN5A consists of 28 exons spanning approximately 80 kb found by Wang et al. (Genomics 34:9-16 (1996)). They described the sequences of all intron/exon boundaries and a dinucleotide repeat polymorphism in intron 16. George et al. (Cytogenet. Cell Genet. 68:67-70 (1995)) mapped the SCN5A gene to 3p21 by fluorescence in situ hybridization, thus making it an important candidate gene for long QT syndrome-3 in 1995. Nav1.5 is responsible for the rapid influx of sodium ions that initiates and propagates action potentials in heart, large peak inward sodium current that underlies excitability and conduction in working myocardium and special conduction tissue. Interventions that modulate sodium current have potent physiologic effects. Mutations in the human SCN5A gene cause the long QT syndrome (LQT) and idiopathic ventricular fibrillation (IVF). Mutations in SCN5A that generate truncated, misprocessed, or dysfunctional proteins produce the Brugada variant of idiopathic ventricular fibrillation. Schott et al. (Nat. Genet. 23:20-21 (1999)) reported a mutation in the SCN5A gene that segregated with progressive cardiac conduction defect (PCCD) in an autosomal dominant manner in a large French family. In a smaller Dutch family, another SCN5A mutation cosegregated with familial nonprogressive conduction defect (Schott et al., 1999). In 2002, Tan et al. (A calcium sensor in the sodium channel modulates cardiac excitability. Nature 415, 442-447 (2002)) demonstrated that calmodulin binds to the carboxy terminal 'IQ' domain of the SCN5A in a calcium-dependent manner. This binding interaction significantly enhances slow inactivation, a channel-gating process linked to life-threatening idiopathic ventricular arrhythmias. In addition, multiple lines of evidence indicate that loss of sodium channel function is also highly arrhythmogenic. For example, chronic therapy with sodium channel blocking drugs in patients convalescing from myocardial infarction increased total mortality and sudden cardiac death (SCD), likely due to arrhythmias.

Brugada syndrome (BrS) is an arrhythmogenic disease characterized by an ECG pattern of ST-segment elevation in the right precordial leads and an increased risk of sudden cardiac death as a result of polymorphic ventricular tachyarrhythmias or ventricular fibrillation. BrS has been associated with SCN5A mutations that cause decreased sodium current (Amin et al., Acta Physiol. Scand., 185:291-301 (2005); Baroudi et al., Can. J. Cardiol. 20:425-30 (2004); Baroudi et al., Circ. Res. 90:E11-E16 (2002); Baroudi et al., Circ. Res. 2001; 88:E78-E83 (2001); and Vatta et al., Mol. Genet. and Metab. 75:317-24 (2002)). A new mutation (MT) in the glycerol-3-phosphate dehydrogenase 1-like (GPD1-L) gene has been reported that causes BrS by reducing $Na^+$ current (London et al., Circulation 116:2260-2268 (2007)). However, the mechanism for this $Na^+$ current reduction is unclear.

The glycerol-3-phosphate dehydrogenase (GPD) family of genes is involved in NADH-dependent energy metabolism. The glycerol-3-phosphate dehydrogenase is involved in shuttling electrons into the mitochondria. In this shuttle, glycerol-3-phosphate acts as a reduced electron carrier that is oxidized to dihydroxyacetone phosphate by an FAD-linked dehydrogenase on the outer surface of the inner membrane (Zubay, Biochemistry, Chapter 10, part II Carbohydrate metabolism and chemical energy, page 401). GPD uses NADH to reduce cytoplasmic dihydroacetone back to glycerol 3 phosphate. GPD1-L and GPD has similar homology (77%) which may indicate that GPD1L has enzymatic similarity to GPD. However, the mechanism to modulate $Na^+$ current is unclear.

Therefore, it is desirable to elucidate the mechanism for sodium channel regulation and to provide modulators to regulate sodium channel current.

SUMMARY OF THE INVENTION

Cardiac arrhythmia is any of a group of conditions in which the electrical activity of the heart is irregular or abnormal (faster or slower than normal). Some arrhythmias are life-threatening and can cause cardiac arrest and sudden death. Others cause aggravating symptoms, such as an awareness of a different heart beat, or palpitation.

It is well know that a reduction in the voltage-gated sodium current is arrhythmogenic. Such reductions are observed in such conditions as heart failure that is associated with arrhythmic risk. For example, very low sodium current is observed in systolic heart failure. The present inventors have discovered that $NAD^+$ increases sodium channel current and sodium channel levels, while NADH reduces sodium channel current and sodium channel levels.

Accordingly, an object of the present invention provides NAD+ and NADH for modulating sodium channel current, thereby reducing arrhythmic risk, including heart failure and ventricular fibrillation.

Another object of the present invention is to reduce arrhythmic risk by increasing the current necessary for proper heart function. Arrhythmic risk as used herein includes heart failure and ventricular fibrillation. This is accomplished by the use of $NAD^+$, as a dietary supplement or a drug, to mitigate arrhythmic risk. The $NAD^+$ can be administered using various routes of drug administration known in the art, preferably intravenously administration.

Another object of the present invention relates to a method for increasing sodium channel current of a cell using $NAD^+$. This method contains contacting $NAD^+$ with the cell or increasing the extracellular or intracellular $NAD^+$ concentration.

The present inventors have also discovered that NADH, the reduced form of $NAD^+$, has the opposite effect on sodium channels, namely decreasing sodium channel current. As such, an object of the present invention relates to a method for using NADH to reduce sodium channel current. This method contains contacting $NAD^+$ with the cell or increasing the extracellular or intracellular $NAD^+$ concentration.

Another object of the present invention relates to a method for alleviating conditions associated with high sodium channel current, such as pain, seizures, and arrhythmias. The method involves administering NADH to an individual in need of pain reduction. Preferably, the NADH is administered intravenously. By reducing sodium channel current, analgesia is induced.

BRIEF DESCRIPTION OF THE DRAWINGS

FIG. 1 shows cell viability testing. Panel A: HEK 293 cell (SCN5A) viability at 24 h as a function of different NADH concentration. Panel B: HEK 293 cell (SCN5A) viability a 24 h as a function of different $NAD^+$ concentration. $P<0.05$ is significant when compared with 0 mol/L/control compared with different doses of $NADH/NAD^+$. *, $P<0.001$

FIGS. 8A-8C show that incubating HEK cells stably expressing SCN5A with 300 μM NADH or $NAD^+$ overnight had opposing effects on peak current. MT GDP1-L reduces $Na^+$ current, and $NAD^+$ reverses the decrease in peak current seen with MT GDP1-L only (FIGS. 8D-8F). Peak current-voltage relationships for the various conditions are shown in FIGS. 8G and 8H, and peak currents at −20 mV are compared in FIGS. 8I and 8J. The number of observations is in parenthesis. **$p<0.001$ FIG. 9A shows peak current-voltage relationships; and FIG. 9B compares peak currents at −20 mV.

Application of 100 μM NADH or NAD+ in the pipette solution resulted in similar changes in Na+ current as did external application. The number of observations is in parenthesis. *p<0.05

Figure 10:
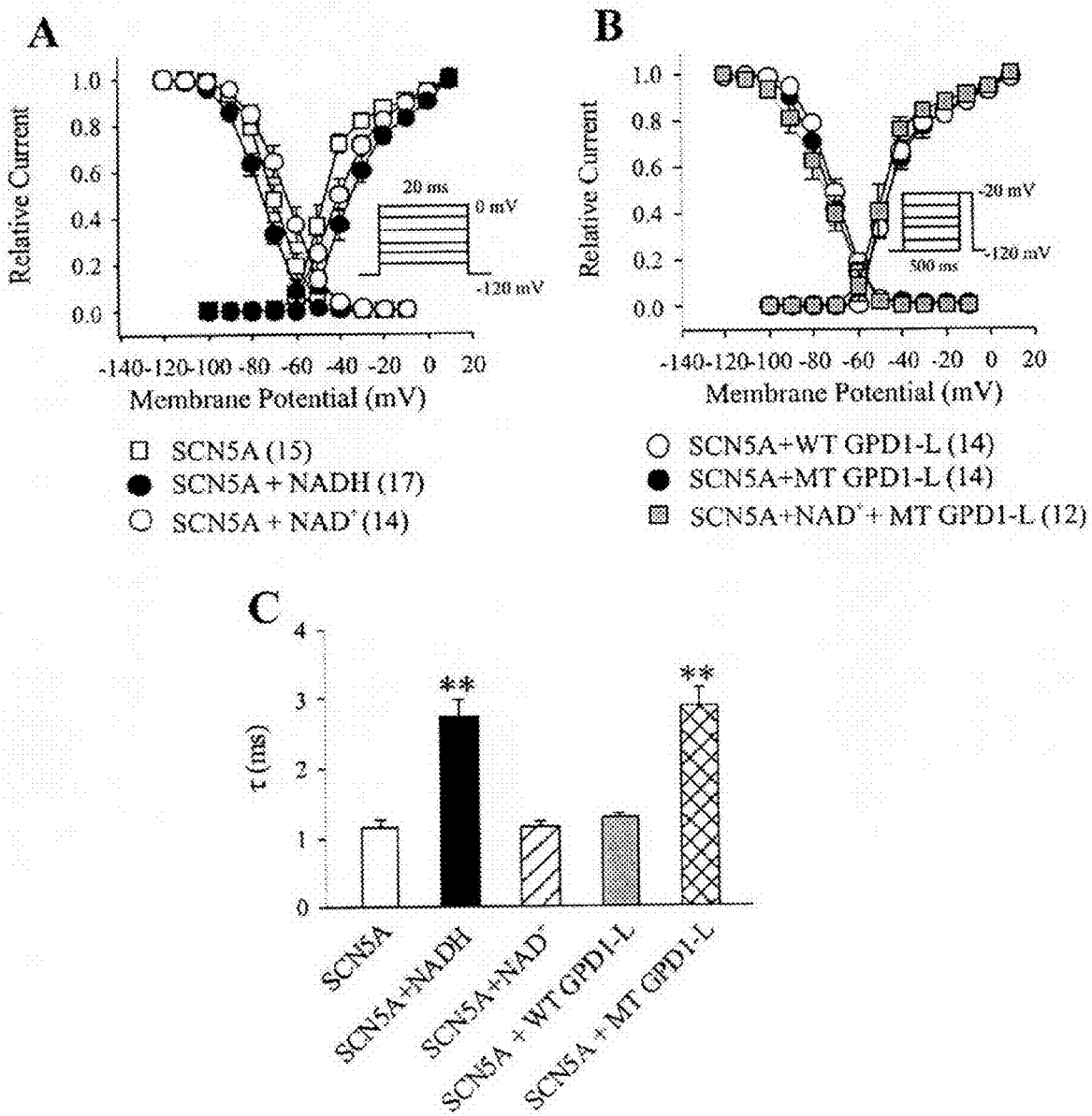

FIG. 10 shows the effects of NADH, NAD+, MT GPD1-L, and WT GPD1-L on Na+ current gating. Steady-state activation and inactivation curves are shown in FIGS. 10A and 10B. The insets show the voltage protocols. Macroscopic inactivation time constants are shown in FIG. 10C. **p<0.001 as compared to the control condition. The number of observations is in parenthesis.

Figure 11:
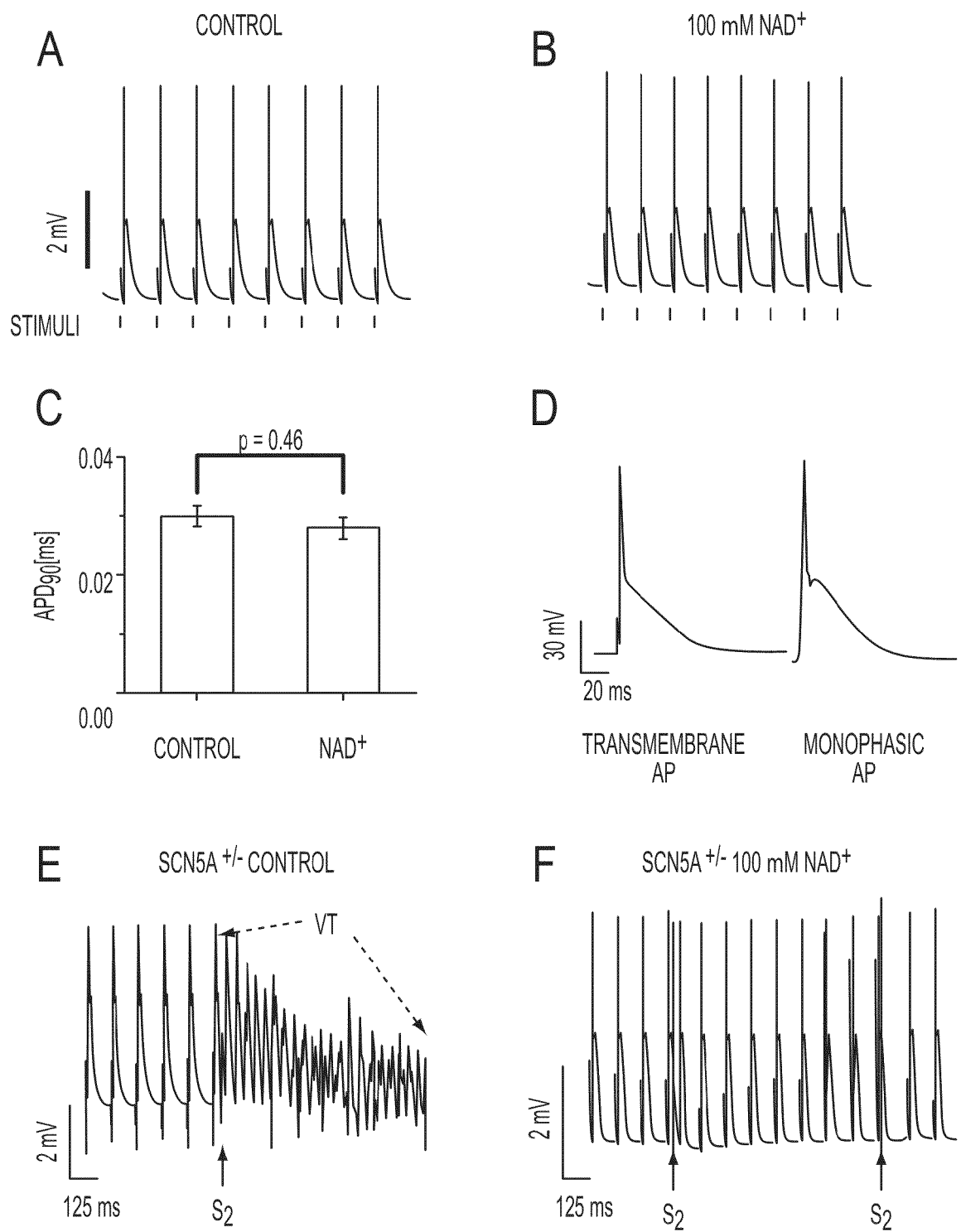

FIG. 11 shows the effect of NAD+ in a model of Brugada Syndrome. FIGS. 11A and 11B show representative traces of MAPs from left ventricular epicardium of Langendorff-perfused SCN5A+/− heart during standard pacing at BCL of 125 ms in the control condition (FIG. 11A) and after 20 min of perfusion with 100 μM NAD+ (FIG. 11B). Vertical lines below the MAPs represent the times when electrical stimulations were delivered. FIG. 11C shows a histogram of $APD_{90}$ in control condition and with 100 μM NAD+. FIG. 11D shows action potentials recorded with the patch-clamp technique in single ventricular myocytes and with the MAP electrode on whole heart. FIG. 11E shows representative MAPs recorded during programmed electrical stimulation (PES) showing PES-induced ventricular tachycardia in SCN5A+/− hearts under control condition. The final six paced beats at 125 BCL ($S_1$) were followed by an extra stimulus ($S_2$) delivered at a $S_1$-$S_2$ interval of 42 ms. PES induced a ventricular tachycardia with cycle length of 20-40 Hz that was sustained for ≈19 seconds. FIG. 11F shows representative trace of PES-induced MAP recording in same SCN5A+/− heart after 20 min perfusion with 100 μM NAD+. $S_2$ stimuli delivered at a 35 ms $S_1$-$S_2$ interval produced a single MAP but failed to induce MAP or VT.

Figure 12:
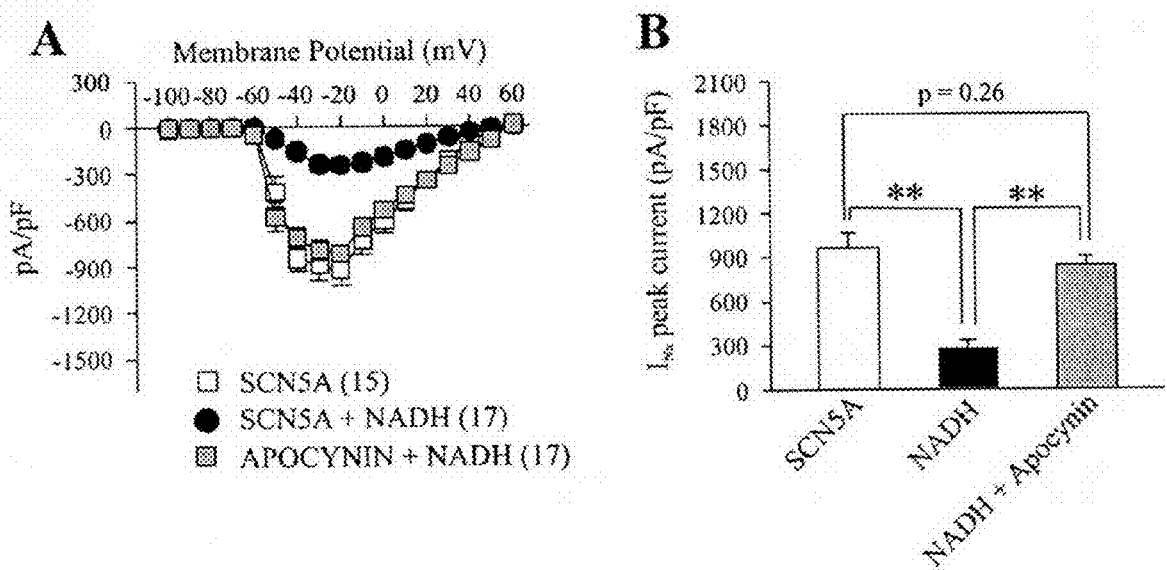

FIG. 12 shows apocynin inhibited the effect of NADH on Na+ currents. FIG. 12A shows current-voltage plots of SCN5A cells treated apocynin, NADH, or both. FIG. 12B compares peak currents at −20 mV. The number of observations is in parenthesis. **p<0.001.

Figure 13:
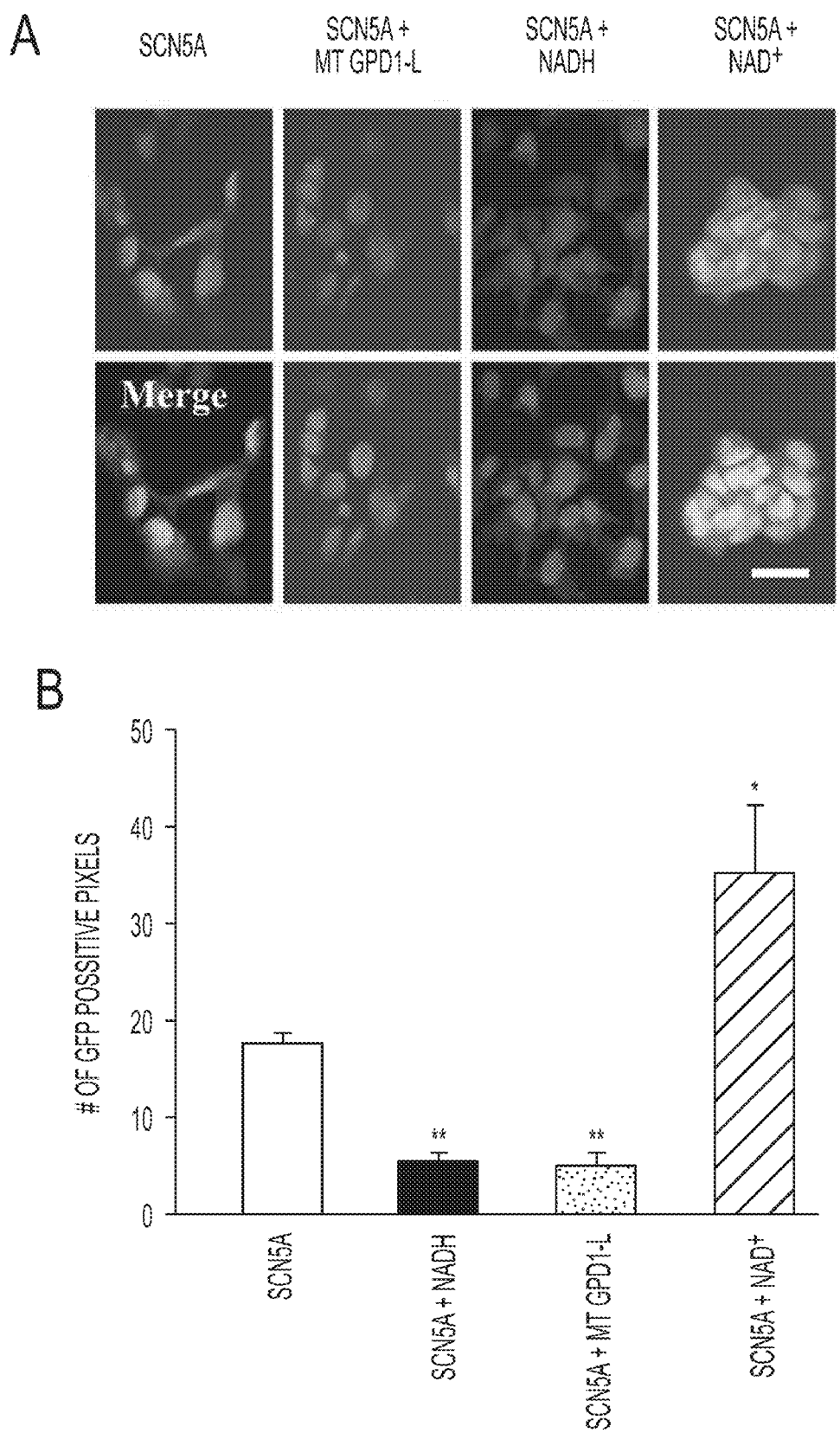

FIG. 13 shows the effects of MT GPD1-L, NADH, and NAD+ on Na+ channel protein. In FIG. 13A, the first line shows confocal microscopy of GFP-tagged SCN5A; and the second line shows the merger of DAPI nuclear staining and GFP channel fluorescence, demonstrating that NADH or co-transfected with MT GPD1-L decreases Na+ channel protein membrane expression in comparison with that in control SCN5A-GFP cells. On the other hand, NAD+ incubation increases Na+ channel protein. Bar=20 μm. FIG. 13B shows quantification of GFP expression which reveals that NADH and MT GPD1-L reduce Na+ channel protein by identical amounts (p=0.66); on the other hand NAD+ exposure raises Na+ channel protein. *p<0.01 and **p<0.001 as compared to the control condition.

DETAILED DESCRIPTION OF THE PREFERRED EMBODIMENTS

An embodiment of the present invention provides compounds that modulate sodium channel activity, such as sodium channel current and sodium channel levels. The compounds of that may be used to modulate sodium channel activity includes the oxidized and reduced forms of nicotinamide adenine dinucleotide. The oxidized form is abbreviated NAD+; and the reduced form is abbreviated NADH. The chemical structure for NAD+ is as follows:

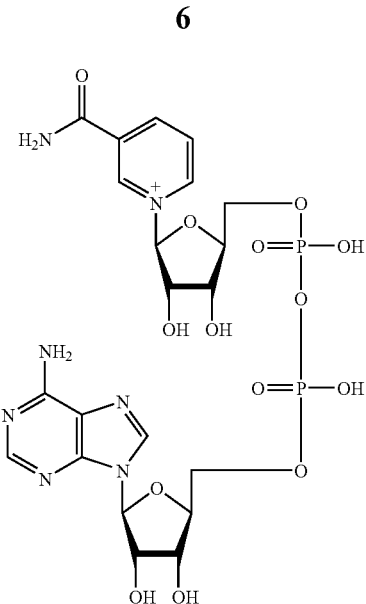

NAD+ can be reduced to form NADH with the following reaction:

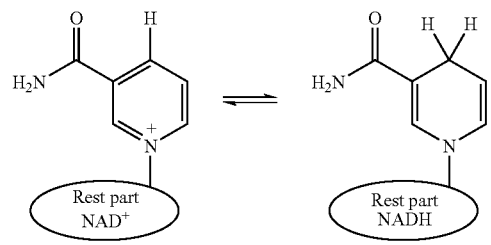

The invention also provides pharmaceutical or dietary supplemental compositions comprising NAD+ or NADH. Accordingly, the compound (NAD+ or NADH), can be formulated for oral or parenteral administration for the therapeutic or prophylactic treatment of diseases or conditions associated with sodium channel activity.

By way of illustration, the compound can be admixed with conventional pharmaceutical carriers and/or excipients and used in the form of tablets, capsules, elixirs, suspensions, syrups, wafers, and the like. Such pharmaceutical compositions contain from about 0.1 to about 90% by weight of the active compound (NAD+ or NADH), and more generally from about 10 to about 30%. The pharmaceutical compositions may contain common carriers and excipients, such as corn starch, gelatin, lactose, sucrose, microcrystalline cellulose, kaolin, mannitol, dicalcium phosphate, sodium chloride, and alginic acid. Disintegrators commonly used in the formulations of this invention include croscarmellose, microcrystalline cellulose, corn starch, sodium starch glycolate and alginic acid.

A liquid composition will generally consist of a suspension or solution of the compound or pharmaceutically acceptable salt in a suitable liquid carrier(s), for example ethanol, glycerine, sorbitol, non-aqueous solvent such as polyethylene glycol, oils or water, optionally with a suspending agent, a solubilizing agent (such as a cyclodextrin), preservative, surfactant, wetting agent, flavoring or coloring agent.

Alternatively, a liquid formulation can be prepared from a reconstitutable powder. For example a powder containing active compound, suspending agent, sucrose and a sweetener can be reconstituted with water to form a suspension; and a syrup can be prepared from a powder containing active ingredient, sucrose and a sweetener.

A composition in the form of a tablet can be prepared using any suitable pharmaceutical carrier(s) routinely used for preparing solid compositions. Examples of such carriers include magnesium stearate, starch, lactose, sucrose, microcrystalline cellulose and binders, for example polyvinylpyrrolidone. The tablet can also be provided with a color film coating, or color included as part of the carrier(s). In addition, active compound can be formulated in a controlled release dosage form as a tablet comprising a hydrophilic or hydrophobic matrix.

A composition in the form of a capsule can be prepared using routine encapsulation procedures, for example by incorporation of active compound and excipients into a hard gelatin capsule. Alternatively, a semi-solid matrix of active compound and high molecular weight polyethylene glycol can be prepared and filled into a hard gelatin capsule; or a solution of active compound in polyethylene glycol or a suspension in edible oil, for example liquid paraffin or fractionated coconut oil can be prepared and filled into a soft gelatin capsule.

Tablet binders that can be included are acacia, methylcellulose, sodium carboxymethylcellulose, poly-vinylpyrrolidone (Povidone), hydroxypropyl methylcellulose, sucrose, starch and ethylcellulose. Lubricants that can be used include magnesium stearate or other metallic stearates, stearic acid, silicone fluid, talc, waxes, oils and colloidal silica.

Flavoring agents such as peppermint, oil of wintergreen, cherry flavoring or the like can also be used. Additionally, it may be desirable to add a coloring agent to make the dosage form more attractive in appearance or to help identify the product.

The compounds of the invention and their pharmaceutically acceptable salts that are active when given parenterally can be formulated for intramuscular, intrathecal, or intravenous administration. A typical composition for intramuscular or intrathecal administration consists of a suspension or solution of active ingredient in an oil, for example arachis oil or sesame oil. A typical composition for intravenous or intrathecal administration consists of a sterile isotonic aqueous solution containing, for example active ingredient and dextrose or sodium chloride, or a mixture of dextrose and sodium chloride. Other examples of aqueous solution are lactated Ringers injection, lactated Ringer's plus dextrose injection, Normosol-M and dextrose, Isolyte E, acylated Ringer's injection, and the like. Optionally, a co-solvent, for example, polyethylene glycol; a chelating agent, for example, ethylenediamine tetracetic acid; a solubilizing agent, for example, a cyclodextrin; and an anti-oxidant, for example, sodium metabisulphite, may be included in the formulation. Alternatively, the solution can be freeze dried and then reconstituted with a suitable solvent just prior to administration.

The compounds of the invention which are active on rectal administration can be formulated as suppositories. A typical suppository formulation will generally consist of active ingredient with a binding and/or lubricating agent such as a gelatin or cocoa butter or other low melting vegetable or synthetic wax or fat.

The active compound is effective over a wide dosage range and is generally administered in a therapeutically effective amount. It, will be understood, however, that the amount of the compound actually administered will be determined by a physician, in the light of the relevant circumstances, including the condition to be treated, the chosen route of administration, the actual compound administered and its relative activity, the age, weight, and response of the individual patient, the severity of the patient's symptoms, and the like. Suitable doses are selected to effect a blood concentration of about 100-300 µM, preferably 100 µM.

According to the invention, a compound can be administered in a single daily dose or in multiple doses per day. The treatment regimen may require administration over extended periods of time, for example, for several days, for from one to six weeks, or longer.

Suitable formulations for use in the present invention can be found in Remington's Pharmaceutical Sciences, Mace Publishing Company, Philadelphia, Pa., 17th ed. (1985).

The compositions of the present invention can be used to treat conditions associated with sodium channel activity, including all disease states and/or conditions that are acknowledged now, or that are found in the future, to be associated with the activity of sodium channels. Such disease states include, but are not limited to, pathophysiological disorders, including hypertension, cardiac arrhythmogenesis, insulin-dependent diabetes, non-insulin dependent diabetes mellitus, diabetic neuropathy, seizures, tachycardia, ischemic heart disease, cardiac failure, angina, myocardial infarction, ventricular fibrillation, transplant rejection, autoimmune disease, sickle cell anemia, muscular dystrophy, gastrointestinal disease, mental disorder, sleep disorder, anxiety disorder, eating disorder, neurosis, alcoholism, inflammation, cerebrovascular ischemia, CNS diseases, epilepsy, Parkinson's disease, asthma, incontinence, urinary dysfunction, micturition disorder, irritable bowel syndrome, restenosis, subarachnoid hemorrhage, Alzheimer disease, drug dependence/addiction, schizophrenia, Huntington's chorea, tension-type headache, trigeminal neuralgia, cluster headache, migraine (acute and prophylaxis), inflammatory pain, neuropathic pain and depression. Conditions associated high sodium channel activity are treated with compositions containing NADH, while conditions associated with low sodium channel activity are treated with compositions containing $NAD^+$.

In a preferred embodiment, the present invention is use to reduce arrhythmic risk, including heart failure and ventricular fibrillation. As previously mentioned, arrhythmic risk is associated with a reduction in the voltage-gated sodium current. As such, compositions comprising $NAD^+$ can be administered to individuals in need of reduced arrhythmic risk to increase sodium channel current, thereby, reducing arrhythmic risk.

Another embodiment of the present invention relates to method for modulating the activity of sodium channels, such as sodium channel current. Compositions containing $NAD^+$ is used to increase sodium channel activity, while NADH is used to reduce sodium channel activity. This method comprises comprising contacting a cell containing the target ion channels with a sodium channel modulating amount of a $NAD^+$ or NADH. The sodium channel modulating amount is preferably about 100-300 mM. The methods provided in this embodiment of the invention can be useful for the diagnosis of conditions that can be treated by modulating sodium channel activity, or for determining if a patient will be responsive to therapeutic agents, which act by inhibiting or activating sodium channel activity.

Without further description, it is believed that one of ordinary skill in the art can, using the preceding description and the following illustrative examples, make and utilize the compounds of the present invention and practice the claimed methods. The following examples are given to illustrate the present invention. It should be understood that the invention is not to be limited to the specific conditions or details described in these examples.

EXAMPLE 1

Methods

Cell Culture and Cell Viability Assays

Human embryonic kidney (HEK) cell line was used for all experiments. A HEK cell line stably expressing a SCN5A-IRES-GFP construct as described in our previous study (Arnold et al., Hearth Rhythm 4:46-53 (2007)) was maintained by antibiotic selection using 0.2 mg/mL Geneticin (G-8168, Sigma-Aldrich). Cells were cultured in Dulbecco's modified Eagle's medium (DMEM; ATCC, Manassas, Va.) with 10% fetal calf serum (ATCC) at 37° C. in 60 mm×15 mm cell culture dishes (Corning Incorporated, Corning, N.Y.) until 70-80% confluence. After reaching confluence, cells were exposed to NADH (Sigma, St. Louis, Mo.) or $NAD^+$ (Sigma) in culture medium for a total of 12-14 h in triplicate. Experiments were repeated three times. After dissociation with 0.125% trypsin-EDTA, 40 µL of 0.4% Trypan-blue (Sigma, St. Louis, Mo.) was added to each well, and a Trypan-blue exclusion viability assay was performed.

Measuring Cellular NADH Levels

Chelex was obtained from Biorad (Hercules, Calif., USA), and a protease inhibitor cocktail was obtained from Sigma (St. Louis, Mo., USA). Cellular NADH level was detected by using the Amplex Red peroxide/peroxidase assay kit (Invitrogen) in HEK 293 cells grown overnight in 12 well cell culture plates co-transfected with GPD1-L (WT or MT). Briefly, this assay is based upon the fact that bacterial NADH oxidase converts NADH into $NAD^+$ and $H_2O_2$. In the presence of peroxidase, $H_2O_2$ is reduced and Amplex red is oxidized, forming an adduct that absorbs light at 570 nm. A brief description of the methodology is described below:

1. Mix Amplex Red working solution (50 µL of 10 mM Amplex Red, 100 µL of 10 U/mL horseradish peroxidase (HRP) in 4.85 mL of 50 mM PBS)) with culture media in a 1:3 ratio.

2. Treat cell with the solution in item 1. Add NADH oxidase (from *Bacillus licheniformis*; Calbiochem) 10 mU/ml final concentration to half the solutions.

3. The NADH signal is the mean Amplex Red signal in NADH oxidase treated cells.

4. After incubation for 14-18 hrs, remove the media, washed twice with ice-cold 1× phosphate buffer (PBS).

5. Scraped and resuspended in 500 µL of lysis buffer (1×PBS (treated for 2 h with 5 g/100 ml Chelex and filtered) containing the protease inhibitors aprotinin (10 µg/ml), leupeptin (0.5 µg/ml), pepstatin (0.7 µ/ml), and PMSF (0.5 mM) (pH 7.4)), cells were transferred into a 1.5 ml clear sterile micro tube and subsequently cells were sonicated (power: 4 watts, using Microson 2425 from Misonix Inc; Farmingdale, N.Y., USA) for 10 s on ice and the membrane pellet was sedimented at 28,000 g for 15 min at 4° C.

6. Supernatants were collected and NADH was determined by the BIO-RAD SmartSpec™ 3000 spectrophotometer (BioRad Laboratories, Hercules, Calif., USA) using Amplex Red absorbance at 570 nm in λ wave length.

Determining the Effects on $Na^+$ Current

HEK cells stably transfected with two different $Na^+$ channel constructs were used, SCN5A-IRES-GFP and SCN5A-GFP fusion constructs. Cloning and establishment of the cell lines has been delineated previously (11). The HEK 293 cell line stably expressing a SCN5A-IRES-GFP construct was maintained by antibiotic selection using Geneticin (G-8168, Sigma-Aldrich) at a concentration of 0.2 mg/mL was used for patch clamp study. GFP was used as a marker to identify cells expressing the cardiac $Na^+$ channel. The cells were cultured in 6 well plates with Dulbecco's Modified Eagle's medium (DMEM), 10% fetal bovine serum and 1% pen-strep. Cells were stored in a 5% $CO_2$ incubator at 37° C. for 1-2 days. GPD1-L (the A280V mutant or wild-type) was transiently co-transfected into HEK 293 cells. GPD1-L vectors have been described in London et al.

The effects of external NADH or $NAD^+$ on sodium current were determined by incubating HEK 293 cells overnight (12-14 h) with $NADH/NAD^+$ (300 µM) added to the media. The effects of internal NADH or $NAD^+$ (100 µM) on sodium current were tested by adding the compounds to the pipette solution.

Cells expressing GFP were tested with the whole cell patch-clamp technique in voltage-clamp mode to measure $Na^+$ current levels. For patch-clamping, HEK cells were plated onto plastic coverslips 2-3 h before the recordings. Glass pipettes were pulled on a Sutter Model P-97 horizontal puller to a resistance of 1-2 MΩ. The glass pipettes were filled with a pipette solution containing (in mmol/L): CsCl 80, Cesium Aspartate 80, EGTA 11, $MgCl_2$ 1, $CaCl_2$ 1, HEPES 10, $Na_2ATP$ 5 and pH 7.4 with CsOH. The bath solution consisted of (in mmol/L): NaCl 130, CsCl 5, $CaCl_2$ 2, $MgCl_2$ 1.2, HEPES 10 and Glucose 5 (titrated to pH 7.4 with CsOH). Once a seal was established, a small amount of suction was applied to obtain the whole cell configuration. A stepped voltage protocol from −100 to +60 mV from a holding potential of −100 mV was applied to establish the presence of voltage-gated $Na^+$ channels. Currents obtained during steps to −10 mV were used for comparison in determining the relative reduction in sodium current. Cells were tested at 25° C. In all recordings, 80% of the series resistance was compensated, yielding a maximum voltage error of ~1 mV. Data were sampled at 10 kHz and later filtered at 5 kHz for analysis. Currents were recorded and analyzed with an Axopatch 200B amplifier, Axon Digidata 1230A A/D converter and pClamp software (Molecular Devices Corporation, Sunnyvale, Calif.).

$Na^+$ Channel Tracking

An SCN5A constructed fused at the C-Terminus to GFP (SCN5A-GFP fusion) was stably transfected in HEK cells and grown on glass bottom 14 mm microwell dishes (MatTek Corporation, Ashland, Mass., USA). A Nikon (Melville, N.Y.) Diaphot 200 inverted microscope with a fluorescent lamp was used to identify cells expressing GFP. Cells expressing GFP were transiently co-transfected with MT GPD1-L or incubated overnight with NADH. Fixation was performed by washing the coverslip three times with DPBS (Dulbecco's Phosphate Buffered Saline 1× of GIBCO) and exposing them to 4% paraformaldehyde in PBS at pH 7.4. Then, 1.0 mL of OS 30 Dow Corning fluid (MatTek Corporation, Ashland, Mass., USA) was added We allowed the dish to sit in the OS 30 for 20 to 30 minutes at room temperature under low light. Immediately before we removed the coverslip, add about 20 to 25 µL of Vectashield (Vector Laboratories, Inc, Burlingame, Calif.). and the sample was sealed with nail polish. Slides were kept in the dark and immediately imaged. GFP was excited at 488 nm with an argon ion 30 mW water-cooled laser was used. GFP fluorescence was observed using a 507 nm narrow bandpass filter and a 60× oil 1.4 NA objective. Quantification was done using ImageJ software.

Statistics

Data are presented as mean±SEM. Significance was determined using two-tailed Student's t-test for paired or unpaired variables, and ANOVA for continuous variables. A value of $P<0.05$ was considered significant.

Results

The Effect of Mutant GPDL on Intracellular NADH Levels.

Given the homology of GPD and GPDL, we hypothesized that GPDL might alter NADH levels in a manner consistent with GPD. NADH levels were measured in cells expressing SCN5A only and cells expressing SCN5A and co-transfected with MT GPD1-L (A280V) and WT GPD1-L (A280A). NADH level was significantly increased in MT GPD1-L (A280V) comparison with WT GPD1-L and SCN5A cell.

NADH and $NAD^+$ Dose Ranging in HEK 293 (SCN5A) Cells:

Because mutant GPDL affected NADH levels, we tested whether alterations in NADH levels could contribute to $Na^+$ current reductions consistent with Brugada syndrome. Prior to doing this, we determined the tolerated concentrations of these agents. SCN5A expressing cells were treated with increased concentrations of NADH and $NAD^+$, and the dose-dependent cell viability was determined. SCN5A cells were tolerant of a wide range of NADH concentrations from 150-300 μmol/L (FIG. 1A). Also, SCN5A-expressing cells were also tolerant a similar range of $NAD^+$ dose concentration (FIG. 1B). Therefore, we selected 300 μmol/L of external NADH and $NAD^+$ for our experiments, where there was no statistically significant increase in cell death over the time course of our experiments for external NADH or $NAD^+$, 24 h exposures.

Effects of NADH and $NAD^+$ on $Na^+$ Current was Similar to that of MT GDPL

Figure 4:
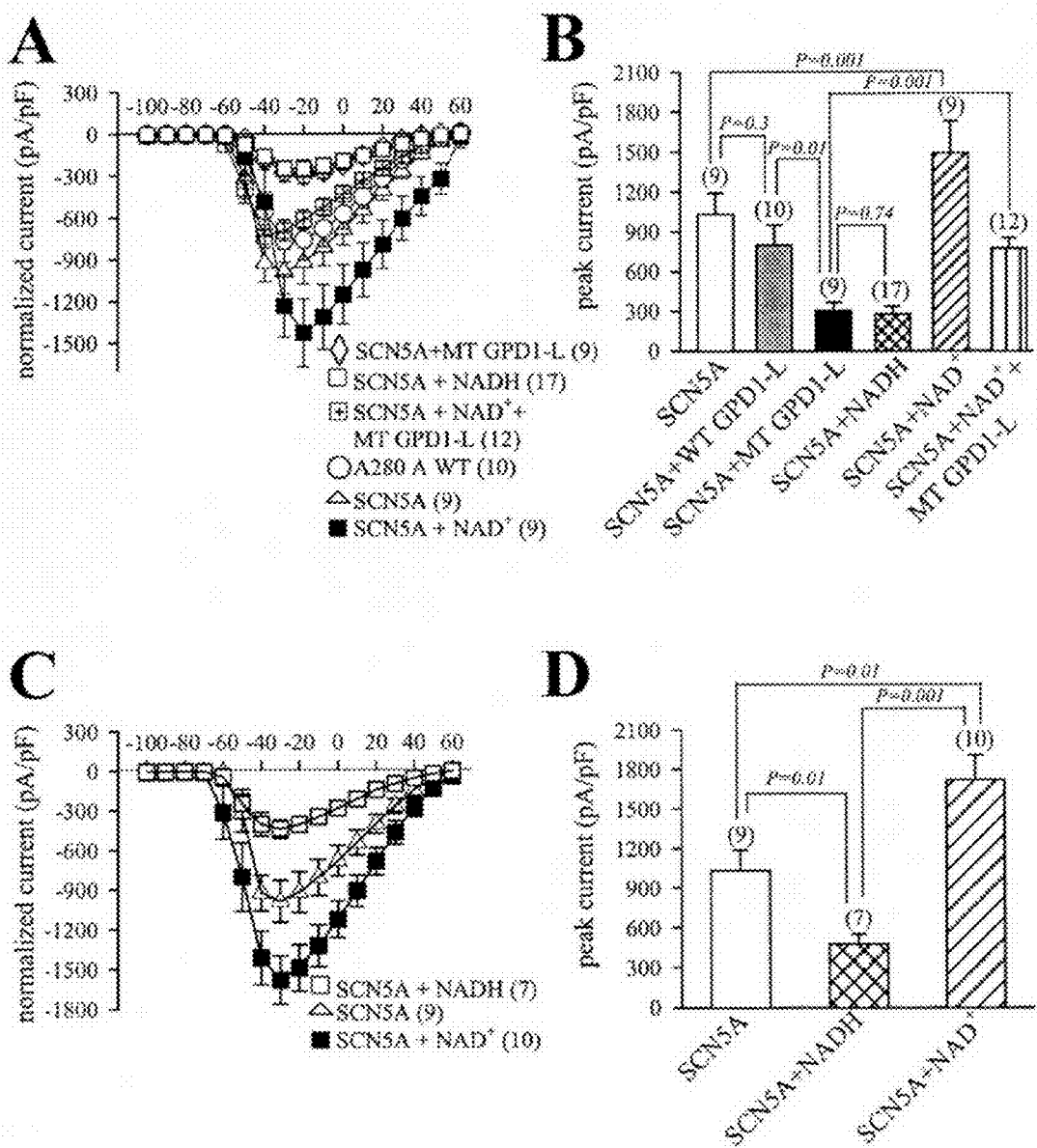
FIG. 4 shows I-V Curve. Average current voltage relationships for SCN5A (n=9), external NADH (n=17)/$NAD^+$ (n=9), A280A (WT GPD1-L) (n=10), A280V (MT GPD1-L) (n=9), and A280V with $NAD^+$ (n=12) (FIG. 4A) and their peak whole-cell $Na^+$ current (FIG. 4B) normalized to the cell capacitance were obtained by measuring peak $Na^+$ currents with a holding potentials from −100 to +60 mV in 10 mV voltage steps. Average current voltage relationships for SCN5A and $NADH/NAD^+$ (100 μM) into internal solution (pipette solution) (FIG. 4C) and their peak whole-cell $Na^+$ current (FIG. 4D) normalized to the cell capacitance were obtained by measuring peak $Na^+$ currents with a holding potentials from −100 to +60 mV in 10 mV voltage steps. Cells incubated NADH and cells expressing A280V have decreased peak $Na^+$ current compared to $NAD^+$, SCN5A and A280A (WT). On the other hand, A280V with $NAD^+$ increased $Na^+$ current at all activation potential compared to A280V expressing cells. Cardiac SCN5A cell co-transfected with MT GPD1-L cause significant ($p<0.001$) decreased in sodium current, incubation overnight with NADH resulted in significant ($p<0.001$) decreased current expression in the wild type (WT) expressing cells and current density was significantly ($p<0.01$) higher for A280V with $NAD^+$ than for A280V expressing cell (FIG. 4B). NADH into pipette solution cause decreased peak $Na^+$ current at all activation potential compared to SCN5A and $NAD^+$ (FIG. 4C), the current density was significantly lower (FIG. 4D) for NADH than for SCN5A ($p=0.01$) and $NAD^+$ ($p=0.01$) and the current density was significantly higher for $NAD^+$ than for SCN5A ($p=0.01$) and NADH ($p=0.01$) (FIG. 4D).

Cells expressing SCN5A and incubated overnight with externally applied NADH (300 μM) showed a reduction in peak current. This was accompanied by a change in macroscopic inactivation. NAD+ largely restored peak current, but did/did not alter macroscopic inactivation. The NADH effect was similar to that of MT GPDL, and the reduction in peak current with this disease-causing mutation was largely prevented by $NAD^+$. Suggesting that MT GPDL was acting through changes in NADH levels, a similar change in inactivation was seen with MT GPDL and with NADH. In FIG. 4, NADH and mutant GDPL have similar effects on the current voltage curve. Cells incubated NADH and cells expressing A280V have decreased peak $Na^+$ current at all activation potential compared to $NAD^+$, SCN5A and A280A (WT). On the other hand A280V with $NAD^+$ increased $Na^+$ current at all activation potential compared to A280V expressing cells. Histogram panel showed (FIG. 4B) that cardiac SCN5A cell co-transfected with MT GPD1-L cause 71.4% decreased in peak sodium current, incubation overnight with NADH resulted in 74.9% decreased peck current expression in the wild type (WT) expressing cells and current density was significantly higher for A280V with $NAD^+$ than for A280V expressing cell.

Incubation overnight with $NAD^+$ caused increased sodium current. In histogram panel A280V and A280V with $NAD^+$ current density revealed that MT GPD1-L (A280V) worked through generating NADH. Instead of overnight incubation with NADH/$NAD^+$ the effect of (100 μM) NADH/$NAD^+$ into internal solution (pipette solution) was tested on $Na^+$ current voltage plots (FIG. 4C) and their peak-amplitude of current density (FIG. 4D). NADH/$NAD^+$ into pipette solution decreased peak $Na^+$ current at all activation potential compared to SCN5A and $NAD^+$ (FIG. 4C) and the current density was significantly lower for NADH than for SCN5A and $NAD^+$ (FIG. 4D). The current density was significantly higher for $NAD^+$ than for NADH and SCN5A (FIG. 4D).

Internal application of $NAD^+$ or NADH had similar effects to those of external application.

Figure 5:
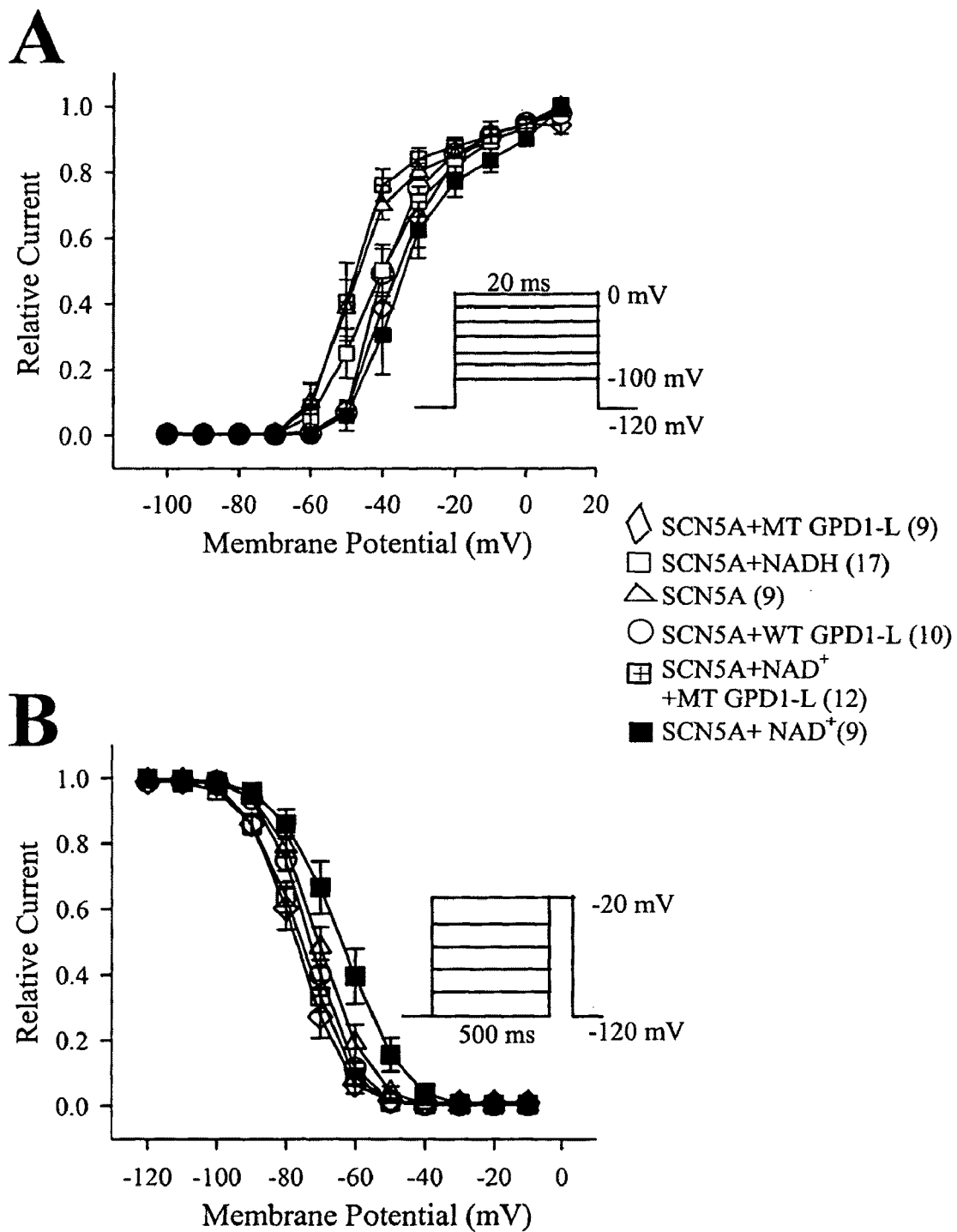
FIG. 5 shows activation and inactivation curves. Activation curve (FIG. 5A) shows the membrane potential at which channels start to open. A shift in the curve to the left or right would indicate a change in activation kinetics. Inactivation curve (FIG. 5B) shows at which membrane potential channels enter into the inactivated state. A shift in the curves would show a change in inactivation kinetics.

The Effects of GDPL and NADH on Gating:

In activation curve (FIG. 5A) for the wild type (WT) GPD1-L (A280A) and mutant (MT) GPD1-L (A280V) the curves are essentially same. A280V with $NAD^+$ activation curve did not shift at all in comparison to SCN5A cell. WT SCN5A in presence of NADH or $NAD^+$ caused activation curves to shift more positive. In activation curve (FIG. 5B) the curves are the same for the WT GPD1-L and mutant (MT) GPD1-L. Mutant GPD1-L (A280V) with $NAD^+$ inactivation curve shifted little negative in comparison to SCN5A cell. However for $NAD^+$, curve was more positive and NADH, curve was more negative compare to SCN5A cell.

Figure 6:
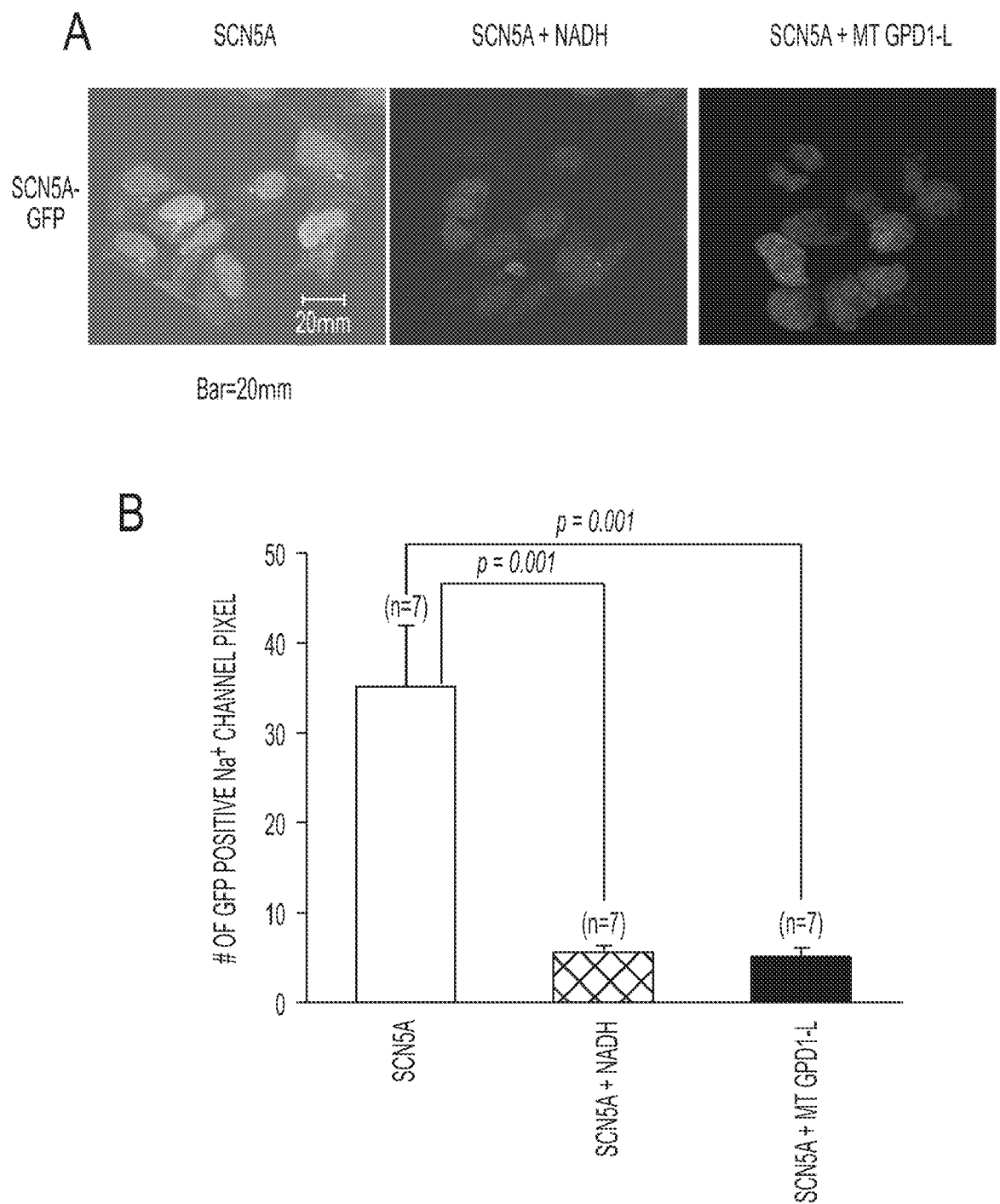
FIG. 6 shows histology studies. Confocal Microscope picture of HEK cell stably transfected with SCN5A-GFP fusion construct and SCN5A-GFP stably transfected cell incubated overnight with NADH and co-transfected with MT GPD1-L (A280V) (FIG. 6A). Quantification of 7 different cells of seven different slides is showing in (FIG. 6B). NADH incubation and MT GPD1-L (A280V) co-transfection causes decreased $Na^+$ channel in comparison to control SCN5A-GFP cell. Quantification data revealed that GFP positive $Na^+$ channel decreased significantly ($p=0.001$) in NADH incubated, MT GPD1-L co-transfected cell (FIG. 6B).

NADH or GPDL Cause a Global Reduction in $Na^+$ Channels (FIG. 6)

Confocal Microscopic pictures revealed that SCN5A-GFP stably transfected cell incubated with NADH and co-transfected with MT GPD1-L (A280V) decreased $Na^+$ channel in comparison to control SCN5A-GFP cell (FIG. 6A). By quantification of 7 different cells of seven different slides it was detected that GFP positive $Na^+$ channel decreased significantly (FIG. 6B) in NADH incubated and MT GPD1-L co-transfected cell.

Conclusion

Brugada Syndrome (BrS) is a life threatening autosomal dominant disorder associated with decreased cardiac sodium channel (SCN5A) current. Recently, we reported a mutation (MT) in the glycerol-3-phosphate dehydrogenase 1-like (GPD1-L) gene causes BrS by reducing $Na^+$ current. Nevertheless, the mechanism for this reduction is unclear. The GPD family of genes is involved in NADH-dependent energy metabolism, and GDP1-L has >75% amino acid homology with GPD. Therefore, we tested the effect on NADH levels of transfecting HEK 293 cells with wild-type (WT) and MT GPD1-L. MT GPD1-L raised cellular NADH level by 3 fold ($p<0.01$). Incubated of HEK cells stably expressing the human cardiac $Na^+$ channel (SCN5A) overnight with 300 μM extracellular NADH decreased whole cell peak conductance by 71.4% ($p<0.001$), while 300 μM extracellular $NAD^+$ caused a 30.3% increase ($p<0.001$, n=9). Neither treatment affected cell viability. Application of 100 μM intracellular NADH had an immediate effect, decreasing $Na^+$ current by 55.5% (p=0.001) at 10 min, while 100 μM intracellular $NAD^+$ showed an increase in current by 66.6% (p=0.01) over the same time frame. The NADH changes were similar to the 69.9% reduction seen when transfecting HEK cells with MT GPD1-L. External $NAD^+$ could prevent the reduction in $Na^+$ current caused by MT GPD1-L. Fluorescent microscopy showed that NADH and MT GPD1-L resulted in statistically significant 6.1 and 6.9 fold reductions in membrane-associated, GFP-tagged $Na^+$ channels. In conclusion, MT GPD1-L raised intracellular NADH, reduced $Na^+$ currents, and decreased membrane associated $Na^+$ channels. These effects were similar to those seen with exogenous NADH, suggesting that GPD1-L may cause BrS by altering NADH levels.

These results hold implications for arrhythmic risk associated with other cardiac metabolic derangements. Because $NAD^+$ increases sodium channel current and level, it could be used as a dietary supplement or a drug to mitigate arrhythmic risk.

EXAMPLE 2

Methods

Cell Viability Assay

As previously described, we maintained a human embryonic kidney (HEK) cell line that stably expresses the human cardiac $Na^+$ channel (SCN5A) with antibiotic selection using 0.2 mg/mL geneticin (G-8168, Sigma-Aldrich, St. Louis, Mo.) (23). Expression of SCN5A was linked to green fluorescent protein (GFP) expression by an internal ribosomal entry site (SCN5A-IRES-GFP). Cells were cultured in Dulbecco's modified Eagle's medium (DMEM; ATCC, Manassas, Va.) with 10% fetal calf serum (ATCC) at 37° C. in 60 mm×15 mm cell culture dishes (Corning Incorporated, Corning, N.Y.) until 70-80% confluency. Then, cells were exposed to NADH or $NAD^+$ (both from Sigma-Aldrich) in culture medium for a total of 24 h. After dissociation with 0.125% trypsin-ethylenediaminetetraacetic acid (EDTA), 40 µL of 0.4% Trypan-blue (Sigma) was added to each well of a 6-well plate, and a Trypan-blue exclusion viability assay was performed. SCN5A cells were tolerant of a wide range of NADH or $NAD^+$ concentrations from 150 to 300 µM (data not shown). Therefore, 300 µM of NADH or $NAD^+$ was used for subsequent experiments because there was no statistically significant increase in cell death over the time course of our experiments (data not shown). All NAD(H) containing solutions were made fresh daily.

Measuring Intracellular NADH

Cellular NADH was detected by using the Amplex Red peroxide/peroxidase assay kit (Invitrogen, Eugene, Oreg.) in HEK 293 cells grown overnight in 12-well cell culture plates incubated with or without 300 µM NADH or co-transfected with wild-type (WT) GPD1-L or mutant (MT) GPD1-L. Briefly, this assay is based upon the fact that bacterial NADH oxidase (EMD Biosciences, Inc. La Jolla, Calif.) converts NADH into $NAD^+$ and $H_2O_2$. In the presence of peroxidase, $H_2O_2$ is reduced, and Amplex red is oxidized, forming an adduct that absorbs light at 570 nm. The Amplex Red working solution, consisting of 50 µL of 10 mM Amplex Red, 100 µL of 10 U/mL horseradish peroxidase in 4.85 mL of 50 mM sodium phosphate buffer at pH 7.4 and 50 mU/mL of NADH oxidase (Bacillus licheniformis; Calbiochem, San Diego, Calif.). The above working solution was added to regular culture media in a 1:3 ratio. Cells were washed twice with ice-cold 1× phosphate buffered saline (PBS), scraped, and resuspended in 500 µL of lysis buffer consisting of 50 mM $Na_3PO_4$ phosphate buffer (pH 7.4). Lysate was treated with 5 g/100 mL Chelex (Biorad, Hercules, Calif.) and protease inhibitors aprotinin (10 µg/mL), leupeptin (0.5 µg/mL), pepstatin (0.7 µg/mL), and phenylmethanesulphonylfluoride (0.5 mM, all from Sigma) for 2 h at room temperature. Then, the lysate was transferred into a 1.5 mL clear sterile tube. The solution was sonicated at 4 W using a Microson 2425 (Misonix Inc; Farmingdale, N.Y.) for 10 s on ice, and the membrane pellet was isolated at 28,000×g for 15 min at 4° C. Supernatant (300 µL) was used for measuring intracellular NADH levels. After 15 min, the absorbance at 570 nm was measured using a Bio-Rad SmartSpec™ 3000 spectrophotometer (BioRad) and reported in arbitrary units (a.u.).

Determining the Effects of Treatments on $Na^+$ Current

Using HEK 293 cells stably expressing the SCN5A-IRES-GFP construct, we measured the effect of treatments on the $Na^+$ current. Cells were cultured in 6-well plates in a 95% $O_2$/5% $CO_2$ incubator at 37° C. WT or MT GPD1-L was transiently transfected into HEK 293 cells as described previously in London et al. Other treatments included extracellular NADH or $NAD^+$ (300 µM) for 14-18 h or NADH or $NAD^+$ (100 µM) in the patch pipette solution. Apocynin (100 µM, Sigma) was added to cells 4-6 h prior to treatment with NADH and continuing for the entire extracellular NADH incubation. $Na^+$ current levels were measured from GFP-expressing cells using the whole-cell patch clamp technique in voltage-clamp mode at room temperature. HEK cells were dissociated by trypsin-EDTA, and replated onto plastic coverslips 2-3 h before the recordings. Glass pipettes were pulled on a Sutter Model P-97 horizontal puller to a resistance of 1-2 MΩ. The glass pipettes were filled with a pipette solution containing (in mM): CsCl 80, cesium aspartate 80, EGTA 11, $MgCl_2$ 1, $CaCl_2$ 1, HEPES 10, and $Na_2ATP$ 5 (adjusted to pH 7.4 with CsOH). The bath solution consisted of (in mM): NaCl 130, CsCl 5, $CaCl_2$ 2, $MgCl_2$ 1.2, HEPES 10 and Glucose 5 (adjusted to pH 7.4 with CsOH). Once a seal was established, a small amount of suction was applied to obtain the whole-cell configuration. A stepped voltage protocol from −100 to +60 mV from a holding potential of −100 mV was applied to establish the presence of voltage-gated $Na^+$ channels. Currents obtained during steps to −10 mV were used for comparison in determining the relative reduction in sodium current. Macroscopic inactivation current decay was best fit using a single exponential equation to determine the time constants (τ). In all recordings, 80% of the series resistance was compensated, yielding a maximum voltage error of ~1 mV. Data were sampled at 10 kHz and later low pass filtered at 5 kHz for analysis. Currents were recorded and analyzed with an Axopatch 200B amplifier, Axon Digidata 1320A A/D converter and pClamp software as described in our previous described (Papadatos, G. A., et al., Proc. Natl. Acad. Sci. U.S.A. 99: 6210-6215 (2002)). To minimize time-dependent drift in gating parameters, all protocols were initiated 5 min. after whole-cell configuration was obtained.

$Na^+$ Channel Tracking

For these experiments, a construct of human SCN5A fused at the C-terminus to GFP (SCN5A-GFP fusion) was stably transfected in HEK cells and grown on the glass bottom of 14-mm microwell dishes (MatTek Corporation, Ashland, Mass., USA). SCN5A-GFP expressing cells were transiently co-transfected with MT GPD1-L or incubated overnight with 300 µM NADH or $NAD^+$. Fixation was performed by washing three times with Dulbecco's PBS (GIBCO, Invitrogen, Carlsbad, Calif.) prior to 4% paraformaldehyde exposure at pH 7.4. Then, 1.0 mL of OS 30 Dow Corning solution (MatTek Corporation, Ashland, Mass.) was added for 20-30 min at room temperature under low light. Before sealing with nail polish, 20-25 µL of Vectashield (Vector Laboratories, Inc, Burlingame, Calif.) was added immediately. For imaging $Na^+$ channels, GFP was excited at 488 nm with an argon ion 30 mW water-cooled laser, and GFP fluorescence was observed using a 507 nm narrow bandpass filter and a 60× oil 1.4 NA objective. Quantification was done using ImageJ software.

SCN5A RNA Abundance

Total RNA from (approximately $2\times10^6$ number of cells/well) was isolated using the TRIzol reagent (Invitrogen, Carlsbad, Calif.). Quantitative SYBR real time RT-PCR was carried out as described using primer pair HE27F and HSCN5AE28A/R (37). β-actin was used as a reference in all cases. The experiment was carried out in triplicate. Briefly, the HEK cell line stably expressing SCN5A-IRES-GFP was as a control. The A280A (wild type) and A280V (mutation) of GPD1-L were transfected into this cell line as described above. NADH (300 µM) or $NAD^+$ (300 µM) was added to the media for 24 h.

Effect of NAD$^+$ in Ventricular Arrhythmogenesis of SCN5A$^{+/-}$ Mouse Heart

Hearts from mice genetically modified to ablate one allele of SCN5A were isolated and Langendorff-perfused (3 ml/min at 37° C.) with Krebs-Henseleit solution (in mM: 119 NaCl, 25 NaHCO$_3$, 4 KCl, 1.2 KH$_2$PO$_4$, 1 MgCl$_2$, 1.8 CaCl$_2$, 10 glucose and 2 sodium pyruvate) and allowed to beat intrinsically for 10 min. Monophasic action potentials (MAPs) were recorded using a MAP electrode (Harvard Apparatus, UK) placed on left ventricular epicardial surface. MAP signals were amplified, band-pass filtered (0.5 Hz to 1 kHz: Neurolog NL900D), digitized (1401, Cambridge Electronic Design, Cambridge, UK) and acquired using Spike 2.5 (Cambridge Electronic Design) at a 5 KHz sampling rate. A custom made, paired-platinum electrode was placed on right ventricle and used to deliver 2 ms (0.5-2 mV, twice the threshold) stimuli (GRASS S48 stimulator) to pace the heart at different intervals. The standard pacing protocol consisted of 8 Hz stimuli (basic cycle length, BCL 125 ms) and was delivered for 20 min to measure MAPs. This was followed by programmed electrically stimulation (PES) consisting of trains of eight paced stimuli at 125 ms BCL ($S_1$) followed by an extra stimulus ($S_2$). Intervals between the 8$^{th}$ $S_1$ and $S_2$ were gradually decreased by 1 ms each sweep until $S_2$ overlaid on the 8$^{th}$ $S_1$. PES was repeated three times before and three times after the drug application in each heart. NAD$^+$ was perfused for 20 min to assess its anti-arrhythmic effect. Selected recordings were imported to Microsoft Excel for further statistical analysis. Average APD$_{90}$ (action potential duration) was calculated by averaging 240 MAPs recorded at three different locations on each heart (80 MAPs at each location). These studies were approved by the Institutional Review Board.

Statistics

All data points are shown as the mean±SEM. Determinations of statistical significance were performed with Student t tests for comparisons of 2 means or with ANOVAs with Student-Newman-Keuls post hoc testing for comparisons of multiple means. A value of p<0.05 was considered statistically significant.

Results

MT GPDL Increases Intracellular NADH

Figure 7:
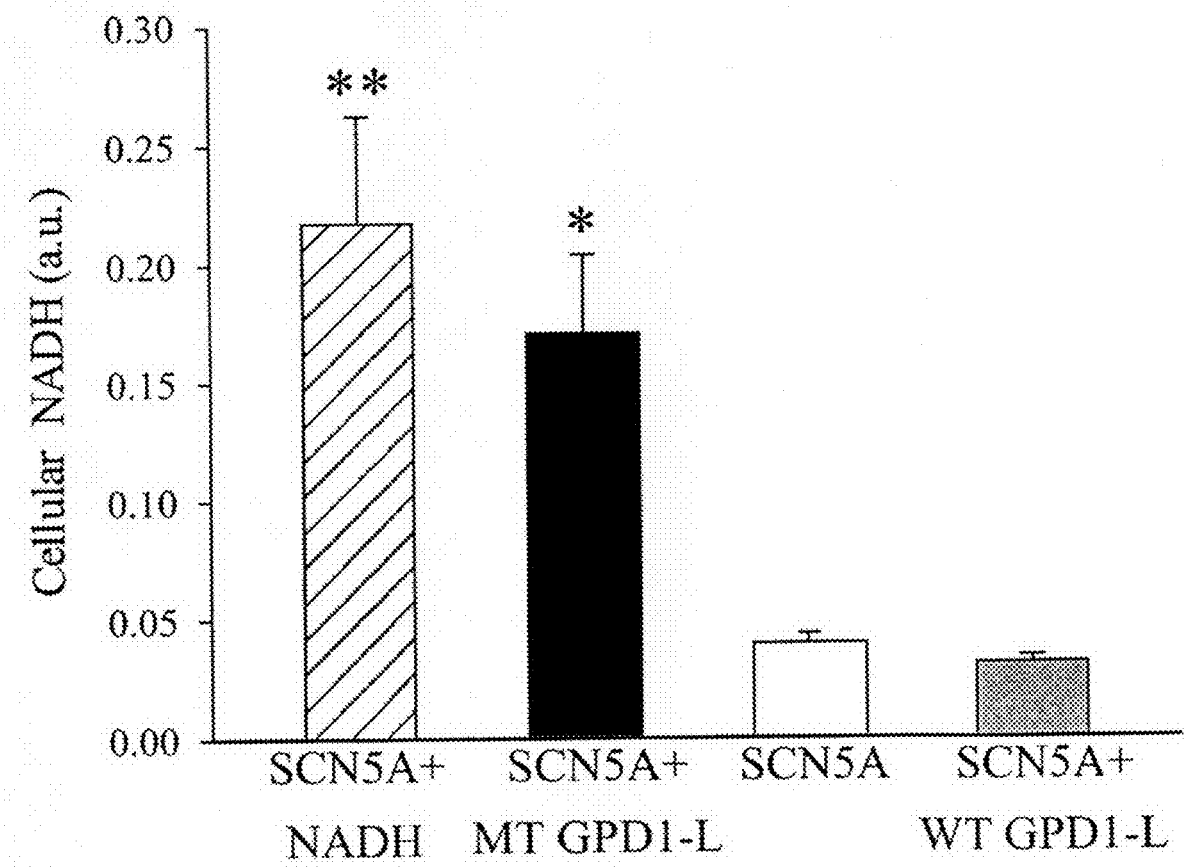
FIG. 7 shows the effects of extracellular NADH, MT GPD1-L, and WT GPD1-L on intracellular NADH. Incubating SCN5A cells with 300 μM NADH or transfected with MT GPD1-L increases intracellular NADH levels in comparison to SCN5A cells alone. *$p<0.01$ and **$p<0.001$.

Given the homology of GPD and GPD1-L and the role of GPD in NADH metabolism, we hypothesized that MT GPD1-L might alter NADH levels. SCN5A cells were co-transfected with WT GPD1-L (A280A) or MT GPD1-L (A280V). WT GPD1-L had no effect on intracellular NADH levels (n=30) as compared to untransfected cells. On the other hand, the NADH level was significantly increased in cells transfected with MT GPD1-L (A280V; p<0.01; n=36). MT GPD1-L raised intracellular NADH level identically to incubation of cells with 300 μM NADH for up to 18 h (n=36; FIG. 7).

NADH and NAD$^+$ Altered Na$^+$ Channel Current

Figure 2:
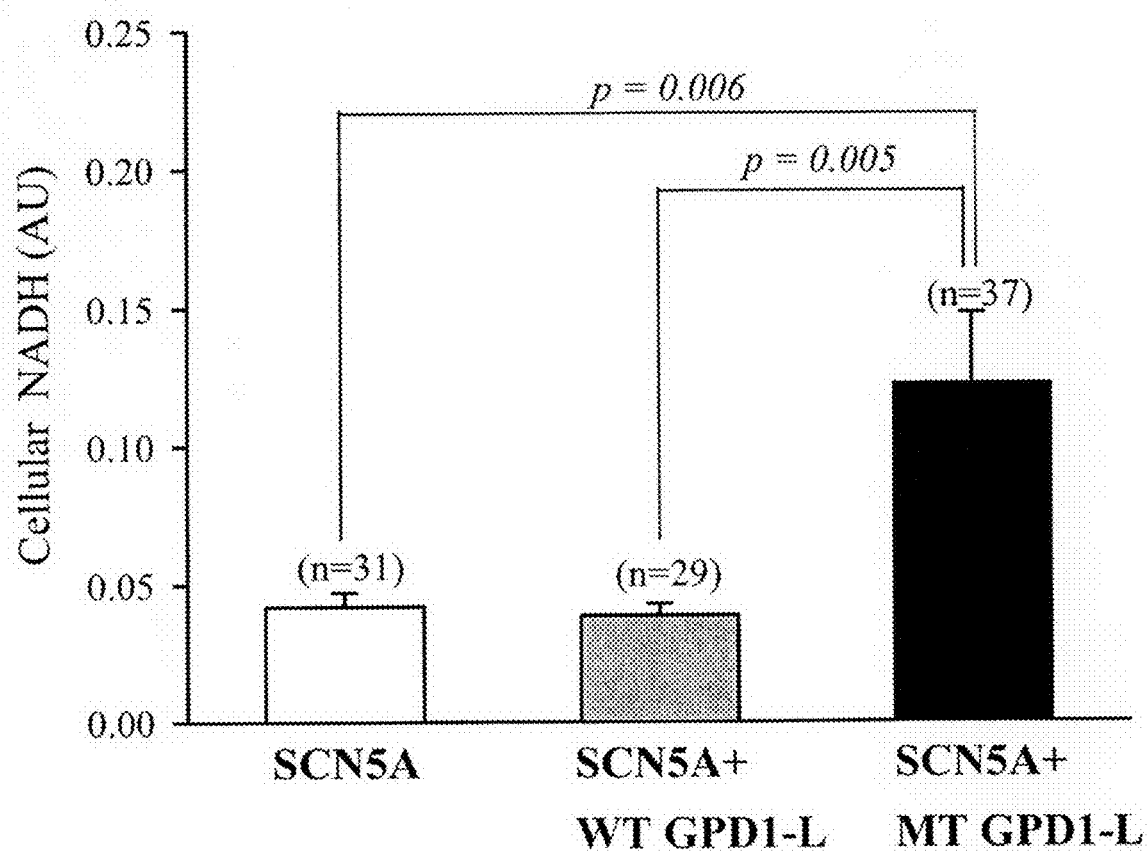
FIG. 2 shows intracellular NADH level measurement. Intracellular NADH level was measured from SCN5A cells (unfilled bar, n=31), SCN5A cells co-transfected with WT GPD1-L (A280A) (dotted bar, n=29) and SCN5A cells co-transfected with MT GPD1-L (A280V) (filled yellow bar, n=37). NADH level was significantly ($p<0.01$) increased in MT GPD1-L (A280V) compare to WT GPD1-L and SCN5A cell.
Figure 3:
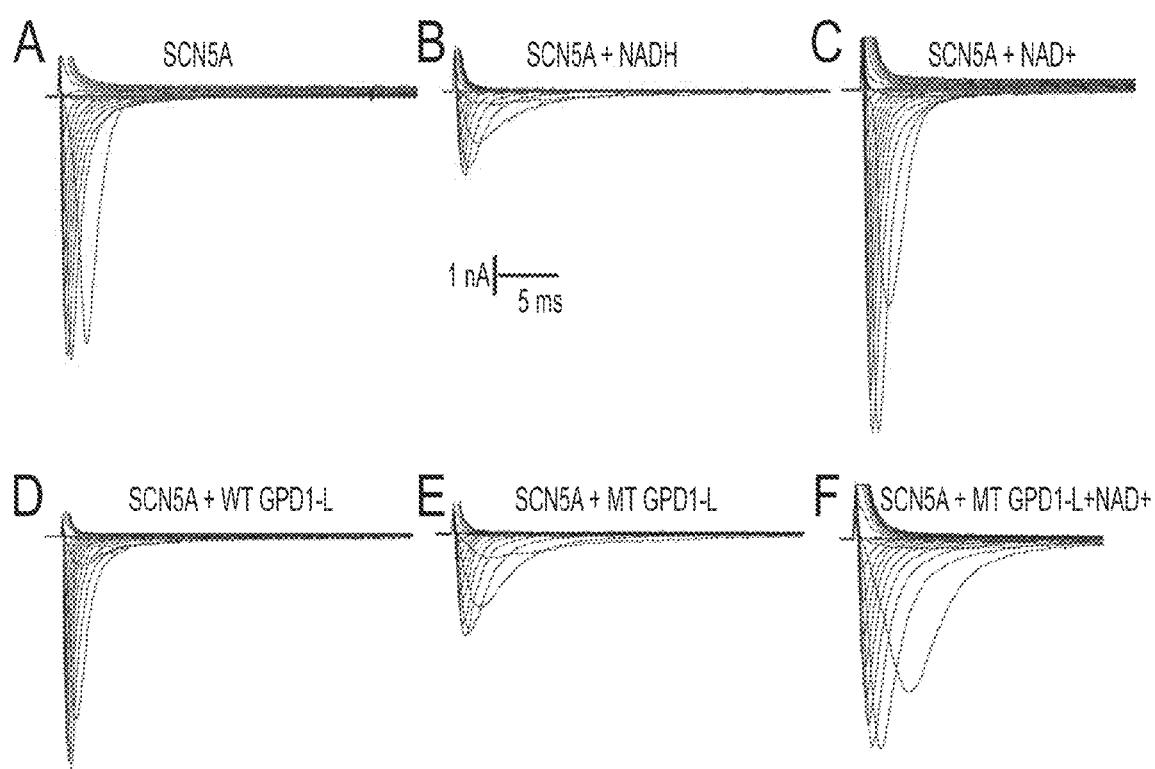
FIG. 3 shows SCN5A, $NADH/NAD^+$, A280A (WT GPD1-L), A280V mutant (MT GPD1-L) and MT GPD1-L $NAD^+$ with current traces. Current trace data of SCN5A, $NADH/NAD^+$ (FIG. 3A, 3B, 3C), the A280A wild type (WT GPD1-L), the A280V mutant (MT GPD1-L), and A280V with $NAD^+$ (FIG. 3D, 3E, 3F). Sodium current traces at various membrane potentials recorded from SCN5A cell and SCN5A cell overnight incubated with NADH (300 μM) and $NAD^+$ (300 μM), (FIG. 3B) current traces showed NADH incubated overnight with HEK cell channels generated a reduced inward $Na^+$ current compared to $NAD^+$ incubated and SCN5A channels cells. The MT GPD1-L revealed lower $I_{Na}$ representative $Na^+$ currents from SCN5A cell co-transfected with the MT GPD1-L (FIG. 3E). MT GPD1-L (A280V) also generated a decreased inward $Na^+$ currents as compared to A280V inhibited with $NAD^+$ (FIG. 3F).
Figure 8:
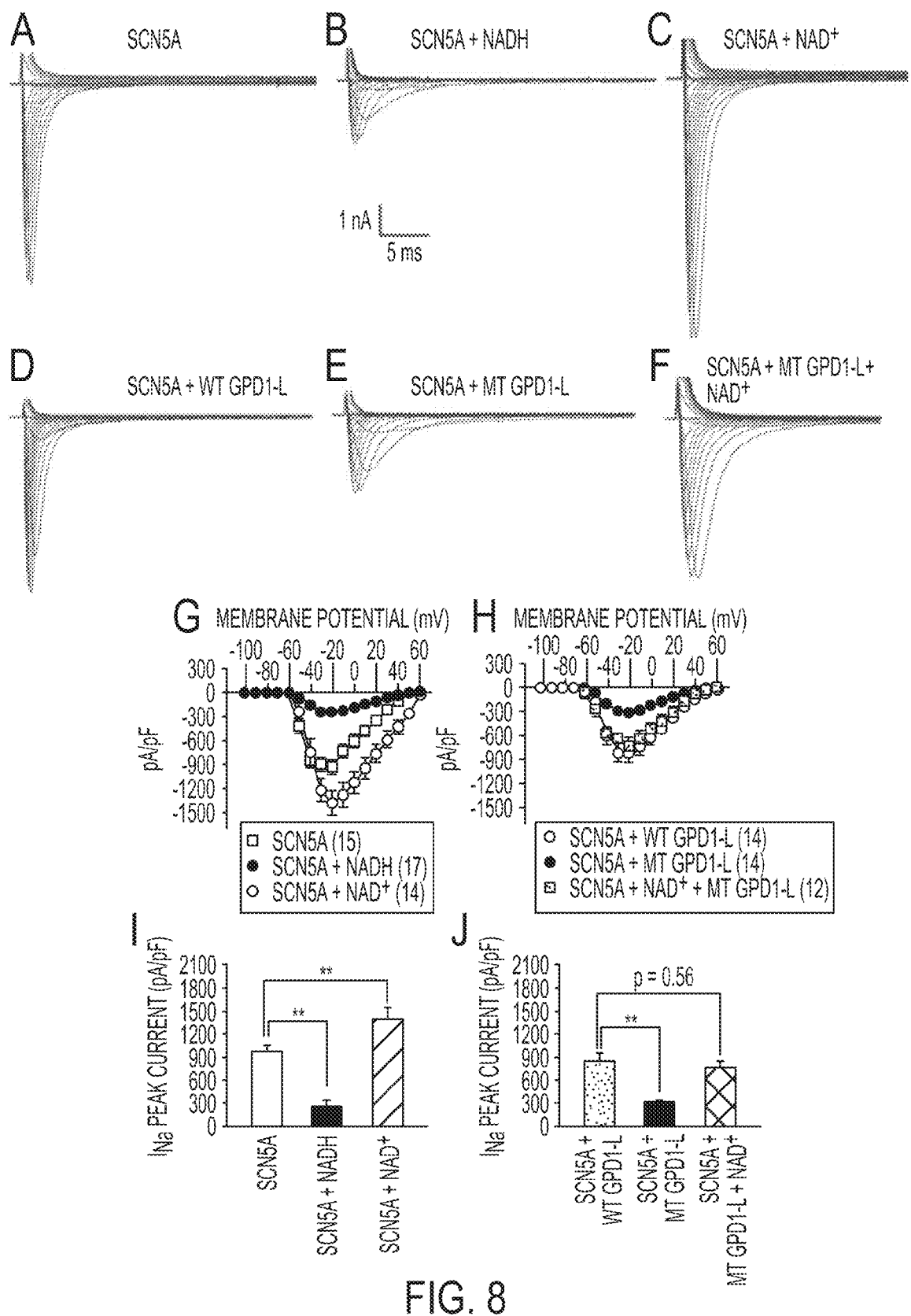
FIG. 8 shows the effects of NADH, $NAD^+$, MT GPD1-L, and WT GPD1-L on $Na^+$ current.

Because MT GPD1-L altered NADH levels, we tested whether increased NADH could contribute to a reduction in Na$^+$ current. NADH (300 μM) applied to cells stably expressing SCN5A reduced Na$^+$ current. On the other hand, NAD$^+$ applied in an identical manner resulted in an increase in peak current (FIG. 8A-8C). The effect of NADH was identical to that of transfecting SCN5A-expressing cells with MT GPD1-L as compared to cells co-expressing the WT GPD1-L (FIGS. 2, D and E). NAD$^+$ prevented the loss of peak current in cells transfected with MT GPD1-L (FIG. 8F). Current-voltage relationships and peak currents at −20 mV for these conditions are compared in (FIG. 8G-8J). Consistent with the lack of effect on intracellular NADH levels, transfection with WT GPD1-L did not alter Na$^+$ channel current. Comparing the effects, MT GPD1-L cause 66.2±3.2% decreased in peak sodium conductance and incubation with NADH resulted in statistically indistinguishable 65.7±6.6% decreased peak current. NAD$^+$ alone increased current density and reversed the effects of MT GPD1-L when applied simultaneously with co-transfection.

Figure 9:
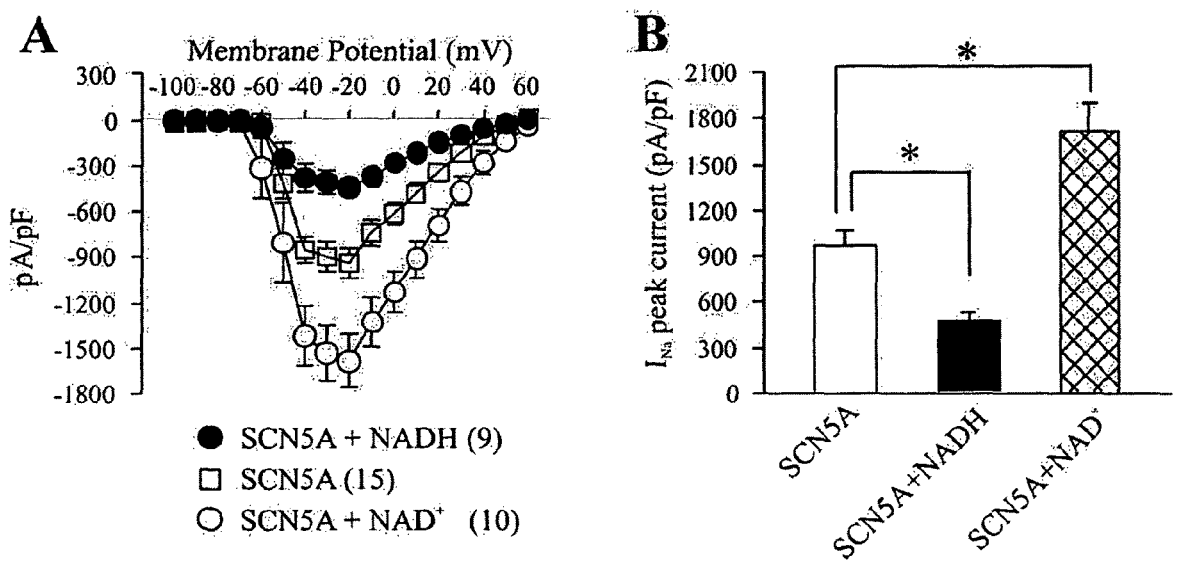
FIG. 9 shows the effects of cytosolic NADH and $NAD^+$ on sodium currents.

Internal application of pyridine nucleotides had identical effects to those of external application of NADH or NAD$^+$. FIG. 9 compares current-voltage curves and peak currents at −20 mV in control cells with those internally applied NADH or NAD$^+$ and shows that NADH reduces peak current at 10 min by 51% (p=0.01), while NAD$^+$ had the opposite effect, raising peak current by 77% (p=0.01).

The changes in peak current with the experimental conditions were largely unexplained by alterations in channel gating. Steady state activation and inactivation curves for SCN5A, NADH-treated, and NAD$^+$-treated cells are compared in FIG. 10A. Steady state activation and inactivation curves for SCN5A cells co-transfected with WT GPD1-L, MT GPD1-L, or MT GPD1-L treated with NAD$^+$ are shown in FIG. 10B. Changes in macroscopic inactivation are compared in FIG. 10C. Macroscopic inactivation was well-fitted with a single exponential equation in each case, and the time constants (τ) of the current decay were increased identically in MT GPD1-L and NADH treated groups as compared to SCN5A (FIG. 10C).

NAD$^+$ Prevents Tachycardia in a Model of Brugada Syndrome

We tested the biological significance of our findings about regulation of the cardiac Na$^+$ channel using an established model of BrS in which one allele of the cardiac Na$^+$ channel has been ablated (SCN5A$^{+/-}$). This model is characterized by a high proclivity towards inducible ventricular tachycardia. MAPs were recorded from six SCN5A$^{+/-}$ and two wild type (WT) mouse hearts. Each MAP consists of a rapid upstroke and smooth repolarization phase giving a triangular shape action potential which was similar to MAPs observed in murine heart (Knollmann et al., Am. J. Physiol. Heart Circ. Physiol. 292:H614-H621 (2007); and Killeen et al. Acta. Physiol. (Oxf) 189:33-46 (2007)). Morphology of monophasic action potentials was similar to transmembrane action potentials recorded by the patch-clamp technique. Perfusion for 20 min with 100 μM NAD$^+$ produced no significant change in MAP duration or morphology (FIG. 11A-11D). Mean values of APD$_{90}$ from six SCN5A$^{+/-}$ hearts after NAD$^+$ perfusion was close to the control value (29.9±1.7 ms in control versus 27.9±1.9 ms in 100 μM NAD$^+$, p=0.46).

To assess the inducibility of ventricular arrhythmia, PES was applied as described in the methods. PES induced multiple episodes of ventricular tachycardia (VT) of varying durations (0.5-48 s) in 6 out of 6 SCN5A$^{+/-}$ hearts (FIG. 11E) but not in WT hearts (n=2). This is consistent with previous observation that a decrease in sodium conductance in mouse ventricle by disrupting SCN5A causes ventricular tachycardia. After 20 min of perfusion with 100 μM NAD$^+$, PES failed to induce VT in 5 out of 6 hearts suggesting an antiarrhythmic property of NAD$^+$ in SCN5A$^{+/-}$ hearts (FIGS. 11E and 11F). The effect of NAD$^+$ was reversible. Multiple episodes of PES-induced VTs were observed in 4 out of 6 hearts when NAD$^+$ was removed.

A Possible Mechanism for the Reduced Na$^+$ Current

Quantitative real-time PCR was undertaken to evaluate the possibility of alterations in transcription or mRNA stability. We did not observe any reductions in SCN5A mRNA abundances when SCN5A HEK cells were transfected with WT or MT GPD1-L or treated with extracellular pyridine nucleotides (data not shown), suggesting that the mechanism for Na⁺ channel reductions was likely to be post-translational.

The NADH oxidase produces oxygen free radicals in an NADH-dependent reaction (Zalba et al., Hypertension 35:1055-1061 (2000)) that is inhibited by apocynin (Javesghani et al., Am. J. Respir. Crit. Care Med. 165:412-418 (2000)). Since MT GPD1-L raised intracellular NADH concentration, we tested whether the NADH oxidase could be involved in mediating the reduction in Na⁺ current. Treatment with apocynin abolished the effect of NADH on Na⁺ current (FIGS. 12A and 12B).

Consistent with the changes in current, confocal microscopy revealed that HEK cells stably expressing the SCN5A-GFP fusion construct and incubated with 300 μM NADH or co-transfected with MT GPD1-L had decreased Na⁺ channel protein in comparison with control SCN5A-GFP cells. On the other hand, 300 μM NAD⁺ incubation caused increased GFP fluorescence, indicating an increased number of channels (FIG. 13A). Quantification of GFP expression revealed that NADH and MT GPD1-L reduced Na⁺ channel protein by identical amounts (p=0.66); on the other hand NAD⁺ exposure raised Na⁺ channel protein (FIG. 13B).

Discussion

Recently, mutations in GPD1-L have been linked to BrS (London et al.), but the mechanism by which mutations of this gene cause reduced Na⁺ current is unknown. We investigated whether GPD1-L might affect Na⁺ channels by altering NADH levels, as does the related protein GPD (Sanyal et al., Circulation 116: II185a-II186a. (Abstr.) (2007)). Here, we show that mutant GPD1-L raises intracellular NADH levels and that increased NADH downregulates Na⁺ current. There are several lines of evidence to suggest that these alterations could account for the reduced Na⁺ current in patients with the GPD1-L mutation tested: 1) the effects of MT GPD1-L were to raise intracellular NADH levels; 2) comparable elevations in intracellular NADH reduced Na⁺ current and protein identically to the effect of MT GPD1-L; 3) WT GPD1-L had no effect on NADH levels or current; and 4) the effects of MT-GPD1-L could be reversed by NAD⁺.

The Mechanism of the NAD(H) Effect

The mechanism whereby pyridine nucleotides have their effect on Na⁺ current is unclear, but some possibilities are suggested by the data. The immediacy of the effect when pyridine nucleotides were added in the pipette solution and the lack of change in mRNA abundances under various experimental conditions suggest that the effect of NAD(H) was post-transcriptional. Post-transcriptional changes are known to regulate the channel. For example, heart failure downregulates SCN5A in a post-transcriptional manner (Zicha et al., J. Mol. Cell. Cardiol. 37: 91-100 (2004)). The changes mediated by NADH and MT GPD1-L are reminiscent of some of the changes seen during acute protein kinase C (PKC) activation, a reduction in current and a prolongation of macroscopic inactivation (Schreibmayer et al., FEBS Lett. 291:341-344 (1991); and Ward et al., J. Physiol. 500:631-642 (1997)). This is consistent with the hypothesis that our effect is mediated by NADH oxidase and that cardiac PKC is activated by oxidative stress (Takeishi et al., Circ. Res. 85:264-271 (1999); Sharma et al., Mol. Cell. Biochem. 219:1-6 (2001); and Brawn et al., Free Radic. Res. 22:23-37 (1995)).

With prolonged exposure, fluorescent tracking of channels demonstrated a decrease in membrane associated channel protein with overnight incubations of NADH or MT GPD1-L. This happened in the absence of changes in Na⁺ channel mRNA abundance, suggesting that, over this time frame, MT GPD1-L was regulating the channel by changes in translation efficiency or protein degradation. This mechanism appears to be somewhat distinct from SCN5A channel mutations that show retention in the sarcoplasmic reticulum, in which surface Na⁺ channel expression can be increased by conditions that improve protein folding (Baroudi et al., Circ. Res. 88:E78-E83 (2001); Pfahnl et al. Heart Rhythm. 4:46-53 (2007); and Kyndt et al., Circulation 104: 3081-3086 (2001)).

Changes in the Na⁺ current induced by pyridine nucleotides are consistent with alterations observed in other channels. Tipparaju et al. (Am. J. Physiol. Cell Physiol. 288: C366-C376 (2005)) have reported that NAD(P)H to NAD(P)⁺ ratio regulates K⁺ currents. In the case of these channels, however, the regulation mostly affects gating rather than peak current. There are multiple other channels regulated by pyridine nucleotides. For example, some transient receptor potential (TRP) currents are increased by NAD⁺ in a manner similar to that seen in our experiments (Heiner et al. 2003. Biochem. J. 371:1045-1053 (2003)). A non-selective cation channel conductance is also increased by NAD⁺ (Herson et al., P J. Physiol. 505:65-76 (1997)). The NADH/NAD⁺ ratio affects Ca²⁺ flux in red blood cells (Alvarez et al., Biochim. Biophys. Acta. 856:408-411 (1986)). Zima et al. (J. Physiol. 555: 727-741 (2004)) show that cytosolic NADH inhibited cardiac sarcoplasmic reticulum Ca²⁺ release channels, while NAD⁺ had activating effects on this channel. Analogously to our results with the Na⁺ channel, NADH has been reported to decrease Ca²⁺-activated K⁺ channel currents, while NAD⁺ increased the current (Park et al., Exp. Physiol. 80:835-842 (1995)).

It is possible that NAD(H) acts directly on the channel or through some intermediaries. Possible intermediaries include the Na⁺ channel β-subunits. Moreover, it is possible that GPD1-L serves as a sensor and acts directly on the channel (London et al.).

Clinical Implications

Our results suggest that NAD⁺ may be a treatment strategy for GPD1-L-mediated BrS, if the acute results are sustained over time. Moreover, the finding that the balance of oxidized and reduced pyridine nucleotides regulates Na⁺ current suggest that the metabolic state of the myocyte may influence Na⁺ channel levels. NADH is known to oscillate with mitochondrial injury, as occurs in ischemic myocardial injury, and mitochondrial injury is associated with increased NADH levels (Aon et al., J. Biol. Chem. 278:44735-44744 (2003); and Di Lisa et al., J. Biol. Chem. 276:2571-2575 (2001)). Given the acute nature of the effects on Na⁺ channels, both of these changes could contribute to reduced Na⁺ current and arrhythmic risk known to exist with ischemia. Moreover, heart failure is associated with increased oxidative stress, reduced NAD⁺, and increased NADH (Choudhary et al., Congest. Heart Fail. 8:148-155 (2002); Pillai et al., J. Biol. Chem. 280:43121-43130 (2005); and Dzhanashiya et al., Bull. Exp. Biol. Med. 138:412-414 (2004)). The increased NADH levels may contribute to the reduced Na⁺ current in this condition (Shang et al., Circ. Res. 101:1146-1154 (2007); Makielski et al., Electrophysiol. Suppl 1:S15-S20 (2006); and Valdivia et al., J. Mol. Cell. Cardiol. 38:475-483 (2005)).

Although certain presently preferred embodiments of the invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

What is claimed is:

1. A method for modulating or for controlling sodium channel current of a cell having an altered sodium current, comprising the step of contacting the cell with a composition containing $NAD^+$ to increase the sodium current or with a composition containing NADH to decrease the sodium current.

2. The method of claim 1, wherein the cell expresses sodium channels.

3. The method of claim 1, wherein the cell expresses SCN5A.

4. The method of claim 1, wherein the $NAD^+$ or NADH concentration is about 100-300 μM.

5. A method for reducing arrhythmic risk associated with an altered sodium current comprising the step of administering a composition containing NAD+ to an individual in need thereof.

6. The method of claim 5, wherein the amount of $NAD^+$ is effective to reduce arrhythmic risk.

7. The method of claim 5, wherein the amount of $NAD^+$ is effective to achieve a $NAD^+$ blood concentration of about 100-300 μM.

8. The method of claim 5, wherein the individual is suffering from arrhythmia.

9. The method of claim 5, wherein the administering step comprises intravenous administration of the composition.

10. The method of claim 5, wherein the composition is selected from the group consisting of a powder, a tablet, a capsule, a solution, and a suspension.

11. The method of claim 5, wherein the $NAD^+$ or NADH is about 0.1 to about 90% by weight of the composition.

12. The method of claim 5, wherein the composition is a solution for intravenous administration.

* * * * *